United States Patent
Rao et al.

(10) Patent No.: US 6,830,927 B2
(45) Date of Patent: Dec. 14, 2004

(54) COMMON NEURAL PROGENITOR FOR THE CNS AND PNS

(75) Inventors: Mahendra S. Rao, Salt Lake City, UT (US); Tahmina Mujtaba, Sandy, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 09/073,881

(22) Filed: May 6, 1998

(65) Prior Publication Data

US 2002/0045251 A1 Apr. 18, 2002

Related U.S. Application Data

(63) Continuation-in-part of application No. 08/852,744, filed on May 7, 1997.

(51) Int. Cl.[7] .................................................. C12N 5/06
(52) U.S. Cl. ........................................ 435/368; 435/377
(58) Field of Search ................................ 435/368, 377, 435/325, 373, 387, 384, 383, 391, 395, 402

(56) References Cited

U.S. PATENT DOCUMENTS

| 5,411,883 A | | 5/1995 | Boss et al. ................ 435/240.2 |
| 5,589,376 A | * | 12/1996 | Anderson et al. ......... 435/240.2 |
| 5,753,506 A | | 5/1998 | Johe ........................... 435/377 |
| 5,824,489 A | * | 10/1998 | Anderson et al. .......... 435/7.21 |

OTHER PUBLICATIONS

Ray et al., J. Neurosci., 14:3548–3564, 1994.*
Rao et al., The Society for Neuroscience, 26th Ann. Meeting, 22:527, Abst. #215.12, 1996.*
Varley et al., Exp. Neurol., 140:84–94, 1996.*
Cattaneo et al., *Nature*, 347:762–765 (1990).

* cited by examiner

Primary Examiner—Gary L. Kunz
Assistant Examiner—Robert C. Hayes
(74) Attorney, Agent, or Firm—Licata & Tyrrell P.C.

(57) ABSTRACT

A method of generating neural crest stem cells involves inducing neuroepithelial stem cells to differentiate in vitro into neural crest stem cells. Differentiation can be induced by replating the cells on laminin, withdrawing mitogens, or adding dorsalizing agents to the growth medium. Derivatives of the peripheral nervous system can be generated by inducing the neural crest stem cells to differentiate in vitro.

4 Claims, 4 Drawing Sheets

COMMON NEURAL PROGENITOR FOR THE CNS AND PNS

CROSS-REFERENCE TO RELATED APPLICATIONS

This application is a continuation-in-part of U.S. application Ser. No. 08/852,744, filed May 7, 1997.

STATEMENT REGARDING FEDERALLY SPONSORED RESEARCH OR DEVELOPMENT

This invention was made with government support under a FIRST award from the National Institutes of Health. The government has certain rights in the invention.

BACKGROUND OF THE INVENTION

This invention relates to multipotent neuroepithelial stem cells, lineage-restricted intermediate precursor cells, and methods of making thereof More particularly, the invention relates to neuroepithelial stem cells that retain the capabilities of self-renewal and differentiation into neurons, astrocytes, and oligodendrocytes. Further, the invention relates to oligodendrocyte-astrocyte-restricted precursor cells that are capable of self-renewal and differentiation into astrocytes and oligodendrocytes, but not neurons. Methods of generating, isolating, and culturing such neuroepithelial stem cells and oligodendrocyte-astrocyte precursor cells are also described. Still further, the invention relates to a methods of generating, isolating, and culturing neural crest stem cells and derivatives of the peripheral nervous system from neuroepithelial stem cells.

Multipotent cells with the characteristics of stem cells have been identified in several regions of the central nervous system and at several developmental stages. F. H. Gage et al., Isolation, Characterization and Use of Stem Cells from the CNS, 18 Ann. Rev. Neurosci. 159–92 (1995); M. Marvin & R. McKay, Multipotential Stem Cells in the Vertebrate CNS, 3 Semin. Cell. Biol. 401–11 (1992); R. P. Skoff, The Lineages of Neuroglial Cells, 2 The Neuroscientist 335–44 (1996). These cells, often referred to as neuroepithelial stem cells (NEP cells), have the capacity to undergo self renewal and to differentiate into neurons, oligodendrocytes, and astrocytes, thus representing multipotent stem cells. A. A. Davis & S. Temple, A Self-Renewing Multipotential Stem Cell in Embryonic Rat Cerebral Cortex, 362 Nature 363–72 (1994); A. G. Gritti et al., Multipotential Stem Cells from the Adult Mouse Brain Proliferate and Self-Renew in Response to Basic Fibroblast Growth Factor, 16 J. Neurosci. 1091–1100 (1996); B. A. Reynolds et al., A Multipotent EGF-Responsive Striatal Embryonic Progenitor Cell Produces Neurons and Astrocytes, 12 J. Neurosci. 4565–74 (1992); B. A. Reynolds & S. Weiss, Clonal and Population Analyses Demonstrate that an EGF-Responsive Mammalian Embryonic CNS Precursor is a Stem Cell, 175 Developmental Biol. 1–13 (1996); B. P. Williams et al., The Generation of Neurons and Oligodendrocytes from a Common Precursor Cell, 7 Neuron 685–93 (1991).

The nervous system also contains precursor cells with restricted differentiation potentials. T. J. Kilpatrick & P. F. Bartlett, Cloned Multipotential Precursors from the Mouse Cerebrum Require FGF-2, Whereas Glial Restricted Precursors are Stimulated with Either FGF-2 or EGF, 15 J. Neurosci. 3653–61 (1995); J. Price et al., Lineage Analysis in the Vertebrate Nervous System by Retrovirus-Mediated Gene Transfer, 84 Developmental Biol. 156–60 (1987); B. A. Reynolds et al., supra; B. A. Reynolds & S. Weiss, supra; B. Williams, Precursor Cell Types in the Germinal Zone of the Cerebral Cortex, 17 BioEssays 391–93 (1995); B. P. Williams et al., supra. The relationship between multipotent stem cells and lineage restricted precursor cells is still unclear. In principal, lineage restricted cells could be derived from multipotent cells, but this is still a hypothetical possibility in the nervous system with no direct experimental evidence.

During development, the neuroepithelial cells that comprise the caudal neural tube differentiate into neurons and glia. Neurons arise from neuroepithelial precursors first and eventually develop unique phenotypes defined by their trophic requirements, morphology, and function. Motoneurons are among the first neurons to develop. V. Hamburger, The Mitotic Patterns in the Spinal Cord of the Chick Embryo and Their Relationship to the Histogenic Process, 88 J. Comp. Neurol. 221–84 (1948); H. O. Nornes & G. D. Das, Temporal Pattern of Neurogenesis in the Spinal Cord of Rat. 1. Time and Sites of Origin and Migration and Settling Patterns of Neuroblasts, 73 Brain Res. 121–38 (1974); J. Altman & S. Bayer, The Development of the Rat Spinal Cord, 85 Adv. Anat. Embryol. Cell Biol. 32–46 (1984); P. E. Phelps et al., Generation Patterns of Four Groups of Cholinergic Neurons in Rat Cervical Spinal Cord: A Combined Tritiated Thymidine Autoradiographic and Choline Acetyltransferase Immunocytochemical Study, 273 J. Comp. Neurol. 459–72 (1988); P. E. Phelps et al., Embryonic Development of Four Subsets of Cholinergic Neurons in Rat Cervical Spinal Cord, 291 J. Comp. Neurol. 9–26 (1990). Motoneurons can be distinguished from other neurons present in the spinal cord by their position and the expression of a number of specific antigens. E. W. Chen & A. Y. Chiu, Early Stages in the Development of Spinal Motor Neurons, 320 J. Comp. Neurol. 291–303 (1992). Tag-1, J. Dodd et al., Spatial Regulation of Axonal Glycoprotein Expression on Subsets of Embryonic Spinal Neurons, 1 Neuron 105–16 (1988), islet-1, J. Erickson et al., Early Stages of Motor Neuron Differentiation Revealed by Expression of Homeobox Gene Islet-1, 256 Science 1555–59 (1992), and p75, W. Camu & C. E. Henderson, Purification of Embryonic Rat Motorneurons by Panning on a Monoclonal Antibody to the Low-Affinity NGF Receptor, 44 J. Neurosci. 59–70 (1992), are expressed uniquely on rat and chick motoneurons early in their development, but are not detectable on other spinal cord cells and, therefore, may serve to distinguish motoneurons from other neural tube cells. Astrocytes, characterized by glial fibrillary acidic protein (GFAP) immunoreactivity, appear soon after; GFAP staining is seen at embryonic day 16 (E16). M. Hirano & J. E. Goldman, Gliogenesis in the Rat Spinal Cord: Evidence for the Origin of Astrocytes and Oligodendrocytes from Radial Precursors, 21 J. Neurosci. Res. 155–67 (1988). Astrocytic cells proliferate and populate the gray and white matter of the spinal cord, and both type 1 and type 2 astrocytes have been identified in the spinal cord. B. C. Warf et al., Evidence for the Ventral Origin of Oligodendrocytic Precursors in the Rat Spinal Cord, 11 J. Neurosci. 2477–88 (1991). Oligodendrocytes appear later and are first detected around birth, though oligodendrocyte precursors may be present as early as E14 based on platelet derived growth factor alpha-receptor (PDGFRA) expression and culture assays. N. P. Pringle & W. D. Richardson, A Singularity of PDGF Alpha-Receptor Expression in the Dorsoventral Axis of the Neural Tube May Define the Origin of the Oligodendrocyte Lineage, 117 Development 525–33 (1993); B. C. Warf et al., supra.

As will be shown herein, NEP cells grow on fibronectin and require fibroblast growth factor (FGF) and an as yet uncharacterized component present in chick embryo extract (CEE) to proliferate and maintain an undifferentiated phenotype in culture. The growth requirements of NEP cells are different from neurospheres isolated from E14.5 cortical ventricular zone cells. B. A. Reynolds et al., supra; B. A. Reynolds & S. Weiss, supra; WO 9615226; WO 9615224; WO 9609543; WO 9513364; WO 9416718; WO 9410292; WO 9409119. Neurospheres grow in suspension culture and do not require CEE or FGF, but are dependent on epidermal growth factor (EGF) for survival. FGF itself is not sufficient for long term growth of neurospheres, though FGF may support their growth transiently. The presently described NEP cells grow in adherent culture, are FGF-dependent, do not express detectable levels of EGF receptors, and are isolated at a stage of embryonic development prior to which it has been possible to isolate neurospheres. Thus, NEP cells appears to represent a multipotent precursor characteristic of the brain stem and spinal cord and peripheral nervous system, while neurospheres may represent a stem cell more characteristic of the cortex.

U.S. Pat. No. 5,589,376, to D. J. Anderson and D. L. Stemple, discloses mammalian neural crest stem cells and methods of isolation and clonal propagation thereof, but fails to disclose cultured NEP cells, cultured lineage restricted precursor cells, and methods of generating, isolating, and culturing thereof. Neural crest cells differentiate into neurons and glia of the peripheral nervous system (PNS), whereas the present neuroepithelial stem cells differentiate into neurons and glia of the central nervous system (CNS) as well as neural crest stem cells and neurons, glia, and other derivatives of the PNS. This patent also fails to disclose generation of neural crest stem cells from neuroepithelial stem cells.

The present invention is necessary to understand how multipotent neuroepithelial stem cells become restricted to the various neuroepithelial derivatives. In particular, culture conditions that allow the growth and self-renewal of mammalian neuroepithelial stem cells are desirable so that the particulars of the development of these mammalian stem cells can be ascertained. This is desirable because a number of tumors of neuroepithelial derivatives exist in mammals, particularly humans. Knowledge of mammalian neuroepithelial stem cell development is therefore needed to understand these disorders in humans. Additionally, the ability to isolate and grow mammalian neuroepithelial stem cells in vitro allows for the possibility of using such stem cells to treat neurological disorders in mammals, particularly humans. Further, such mammalian neuroepithelial stem cells can be used therapeutically for treatment of certain diseases, e.g. Parkinson's Disease, such as by transplantation of such cells into an afflicted individual. Moreover, such cells can still further be used for the discovery of genes and drugs that are useful for treating certain diseases. For example, novel genes can be identified by differential display or subtractive hybridization or other screening strategies. Still further, pure NEP stem cell populations according to the present invention can be used to generate and screen antibodies that are specific for these specific cells.

U.S. Ser. No. 08/909,435, filed Jul. 4, 1997, for Isolation of Lineage-Restricted Neuronal Precursors, relates to lineage-restricted precursor cells and methods of making thereof In particular, these cells are neuronal restricted precursors (NRPs) isolated from embryos or NEP stem cells. These neuronal restricted precursors are capable of self-renewal and differentiation into neurons, but not glia (i.e. astrocytes and oligodendrocytes), of the central nervous system. This application is hereby incorporated by reference.

U.S. Ser. No. 08/980,850, filed Nov. 29, 1997, for Lineage Restricted Glial Precursors from the Central Nervous System, relates to glial restricted precursor cells (GRPs) capable of differentiating into oligodendrocytes and two types of astrocytes. These GRPS can also be isolated from embryos or NEP stem cells. This application is also hereby incorporated by reference.

In view of the foregoing, it will be appreciated that isolated populations of mammalian neuroepithelial stem cells and lineage restricted glial precursor cells and methods of generating, isolating, and culturing such cells would be a significant advancement in the art. It will also be appreciated that a method of generating, isolating, and culturing neural crest stem cells and cells of the peripheral nervous system would also be a significant advancement in the art.

BRIEF SUMMARY OF THE INVENTION

It is an object of the present invention to provide isolated (pure) populations of mammalian neuroepithelial stem cells and their progeny in feeder-cell-independent adherent cultures.

It is also an object of the invention to provide populations of mammalian lineage-restricted glial precursor cells and their progeny in feeder-cell-independent adherent cultures.

It is another object of the invention to provide methods of generating, isolating, and culturing mammalian neuroepithelial stem cells and lineage restricted glial precursor cells and their progeny.

It is still another object of the invention to provide methods for the growth and regeneration of neuroepithelial stem cells and lineage restricted glial precursor cells in feeder-cell-independent adherent cultures.

It is yet another object of the invention to provide a method for the generation of lineage restricted glial precursor cells from neuroepithelial stem cells.

It is a still further object of the invention to provide pure differentiated populations of cells derived from neuroepithelial stem cells and lineage restricted glial precursor cells.

It is yet another object of the invention to provide cDNA and cDNA libraries from pure differentiated populations derived from neuroepithelial stem cells and lineage restricted glial precursor cells.

It is still another object of the invention to provide antibodies specific to NEP cells and lineage restricted glial precursor cells.

It is also an object of the invention to provide a method of generating, isolating, and culturing neural crest stem cells and cells of the peripheral nervous system from NEP cells.

These and other objects can be achieved by providing an isolated, pure population of mammalian CNS neuroepithelial stem cells wherein the cells are capable of self-renewal and proliferation in a feeder-cell-independent adherent culture medium and of differentiation to CNS neuronal or glial cells. Preferably, such neuroepithelial stem cells express nestin, but do not express polysialated neural cell adhesion molecule (N-CAM), glial fibrillary acidic protein (GFAP), sulfatide (O4), neurofilament (NF), choline acetyl transferase (ChAT), intermediate filament ($\beta$-III tubulin), ganglioside (monoclonal antibody A2B5), or galactocerebroside (Gal-C) immunoreactivities. It is also preferred that such CNS neuronal cells do not express intermediate filament ($\mu$-III tubulin) and neurofilament 68 (NF68), choline acetyl transferase (ChAT), glial fibrillary acidic protein (GFAP), ganglioside (monoclonal antibody A2B5), sulfatide (O4), or galactocerebroside (Gal-C) immunoreactivies. The neuroepithelial stem cells preferably are further capable of differentiation to glial-restricted precursor cells. Such glial-restricted precursor cells are preferably capable of self-renewal and proliferation in a feeder-cell-independent adherent culture medium and of differentiation to CNS glial cells but not to CNS neuronal cells. These glial-restricted precursor cells preferably express nestin and ganglioside (monoclonal antibody A2B5) immunoreactives, but do not express glial fibrillary acidic protein (GFAP), sulfatide O4), or galactocerebroside (Gal-C) immunoreactivies.

Another illustrative embodiment of the invention comprises an isolated, pure population of mammalian CNS glial-restricted precursor cells, wherein the glial-restricted precursor cells are capable of self-renewal and proliferation in a feeder-cell-independent adherent culture medium and of differentiation to CNS glial cells but not to CNS neuronal cells.

Still another illustrative embodiment of the invention comprises a method of isolating a pure population of mammalian CNS neuroepithelial stem cells wherein the cells are capable of self-renewal in feeder-cell-independent adherent culture medium and of differentiation to CNS neuronal or glial cells, comprising the steps of:

(a) removing a neural tube from a mammalian embryo at a stage of embryonic development after closure of the neural tube but prior to differentiation of cells in the neural tube;

(b) dissociating cells comprising the neural tube removed from the mammalian embryo;

(c) plating the dissociated cells in feeder-cell-independent culture on a substratum and in a medium configured for supporting adherent growth of the neuroepithelial stem cells, wherein the medium comprises effective amounts of fibroblast growth factor and chick embryo extract; and (d) incubating the plated cells at a temperature and in an atmosphere conducive to growth of the neuroepithelial stem cells.

Yet another illustrative embodiment of the invention comprises a method of isolating a pure population of mammalian CNS glial-restricted precursor cells wherein the cells are capable of self-renewal in feeder-cell-independent adherent culture medium and of differentiation to CNS glial cells but not CNS neuronal cells, comprising the steps of:

(a) isolating a population of mammalian CNS neuroepithelial stems cells;

(b) incubating the neuroepithelial stem cells in a medium configured for supporting growth of the neuroepithelial stem cells except for lacking an effective amount of chick embryo extract for a period of time sufficient for the cells to begin differentiating;

(c) subjecting the incubated cells to specific antibody capture using an antibody characteristic of glial-restricted precursor cells to result in a captured subpopulation of cells; and (d) incubating the captured subpopulation of cells in a medium configured for supporting growth thereof comprising effective amounts of fibroblast growth factor and platelet derived growth factor.

Yet another illustrative embodiment of the invention comprises a method of generating a population of mammalian motoneurons comprising the steps of:

(a) isolating a population of mammalian CNS neuroepithelial stems cells;

(b) incubating the neuroepithelial stem cells in a medium that promotes cell proliferation and neuronal differentiation for a period of time sufficient for the cells to begin differentiating; and (c) isolating motoneurons from said differentiating cells. A preferred medium comprises the use of laminin-coated plates and NEP medium lacking an effective amount of chick embryo extract.

A method for generating mammalian neural crest stem cells comprises inducing neuroepithelial stem cells to differentiate in vitro, thereby generating said neural crest stem cells. Inducing the differentiation of the NEP cells can be carried out by replating the neuroepithelial stem cells on a laminin-coated substrate, withdrawing mitogens such as FGF or chick embryo extract, or adding a dorsalizing agent to the cells. Preferred dorsalizing agents are bone morphogenetic proteins, such as BMP-2, BMP-4, and BMP-7.

A method of generating cells of the peripheral nervous system comprising the steps of:

(a) inducing neuroepithelial stem cells to differentiate in vitro, thereby generating neural crest stem cells;

(b) inducing said neural crest stem cells to differentiate in vitro, thereby generating peripheral nervous system cells.

Neural crest stem cells can be induced to differentiate according to methods well known in the art, such as are described in U.S. Pat. No. 5,589,376, hereby incorporated by reference.

DETAILED DESCRIPTION

Figure 1:
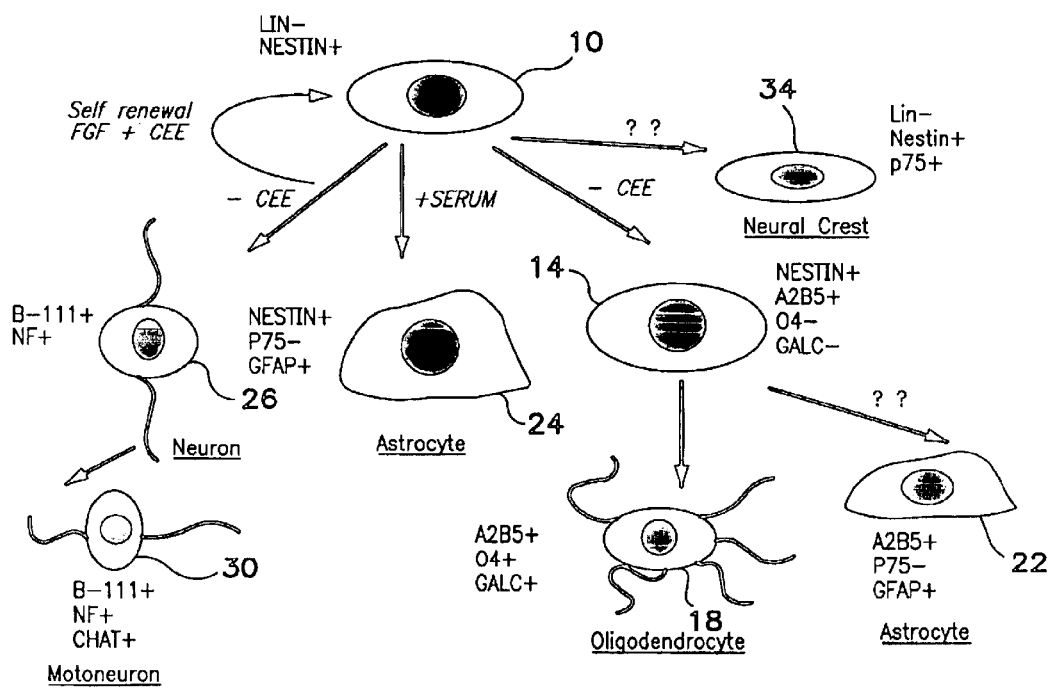
FIG. 1 shows a summary of the immunoreactivities of NEP cells and their progeny.

Before the present neuroepithelial stem cells, glial-restricted precursor cells, and methods of making thereof and methods of making neural crest stem cells and PNS derivative cells are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to "an embryo" includes reference to two or more embryos, reference to "a mitogen" includes reference to a mixture of two or more mitogens, and reference to "a factor" includes reference to a mixture of two or more factors.

In describing and claiming the present invention, the following terminology will be used in accordance with the definitions set out below.

As used herein, "self renewal" refers to the capability of a neuroepithelial stem cell to divide to produce two daughter cells, at least one of which is a multipotent neuroepithelial stem cell.

As used herein, "clonal density" and similar terms mean a density sufficiently low enough to result in the isolation of single, non-impinging cells when plated in a selected culture dish. An illustrative example of such a clonal density is about 225 cells/100 mm culture dish.

As used herein, "feeder-cell-independent adherent culture" or similar terms mean the growth of cells in vitro in the absence of a layer of different cells that generally are first plated on a culture dish to which the cells from the tissue of interest are then added. In feeder cell cultures, the feeder cells provide a substratum for the attachment of cells from the tissue of interest and additionally serve as a source of mitogens and survival factors. The feeder-cell-independent adherent cultures herein use a chemically defined substratum, for example fibronectin, and mitogens or survival factors are provided by supplementation of the liquid culture medium with either purified factors or crude extracts from other cells or tissues. Therefore, in feeder-cell-independent cultures, the cells in the culture dish are primarily cells derived from the tissue of interest and do not contain other cell types required to support the growth of cells derived from the tissue of interest.

As used herein, "effective amount" means an amount of a growth or survival or other factor that is nontoxic but sufficient to provide the desired effect and performance. For example, an effective amount of FGF as used herein means an amount selected so as to support self renewal and proliferation of NEP cells when used in combination with other essential nutrients, factors, and the like.

The present invention is illustrated using neuroepithelial stem cells isolated from the rat. The invention encompasses all mammalian neuroepithelial stem cells and is not limited to neuroepithelial stem cells from the rat. Mammalian neuroepithelial stem cells can be isolated from human and non-human primates, equines, canines, felines, bovines, porcines, ovines, lagomorphs, and the like.

The present invention concerns an embryonic spinal cord stem cell, termed NEP cell, derived from caudal neuroepithelium, that requires fibroblast growth factor (FGF) and chick embryo extract (CEE) to proliferate and self renew. NEP cells are characterized by: (1) the expression of nestin, (2) the absence of lineage markers, (3) ability to be maintained in an undifferentiated state in culture, (4) the ability to self renew, and (5) the ability to grow in clonal culture. Under appropriate environmental conditions, NEP cells differentiate into the three principal types of cell in the CNS, neurons, astrocytes, and oligodendrocytes. FIG. 1 presents a model for spinal cord differentiation. This model is similar to that proposed for hematopoiesis and for differentiation of neural crest (see review by D. J. Anderson, The Neural Crest Lineage Problem: Neuropoiesis?, 3 Neuron 1–12 (1989)). According to this model, NEP cells 10 represent a homogeneous population of cells in the caudal neural tube that express nestin (nestin$^+$) but no other lineage marker (lin$^-$). These cells divide and self renew in culture and generate differentiated phenotypes. Previous data have suggested intermediate dividing precursors with a more restricted potential. R. H. Miller & V. Szigeti, infra; B. C. Warf et al., supra; N. P. Pringle & W. D. Richardson, supra; J. Ray & F. Gage, Spinal Cord Neuroblasts Proliferate in Response to Basic Fibroblast Growth Factor, 14 J. Neurosci. 3548–64 (1994). Such precursors include those precursors 14 that generate oligodendrocytes 18 and type 2 astrocytes 22, bipotent astrocyte and neuronal precursors (not shown in FIG. 1), as well as neuronal progenitors that generate several kinds of neurons (not shown in FIG. 1). The model therefore suggests that the multipotent precursors (NEP cells) generate differentiated cells (i.e., oligodendrocytes 18, type 2 astrocytes 22, type 1 astrocytes 24, neurons 26, and motoneurons 30) through intermediate precursors. Consistent with this model are the results presented herein showing the existence of cells with a restricted proliferative potential.

FIG. 1 shows that motoneurons arise from a common NEP precursor. The experiments described herein show that low affinity neurotrophin receptor (p75) immunoreactive, choline acetyl transferase (ChAT) positive cells arise in mixed cultures along with other cells of the spinal cord. No clone consisting exclusively of p75/ChAT immunoreactive cells was identified, indicating that, at the age the clones were analyzed, committed motoneuron precursors were not present. The observation that motoneurons arise from a common NEP precursor are consistent with results obtained in chick neural tube experiments. E.g., M. Bronner-Fraser & S. E. Fraser, Cell Lineage Analysis Slows Multipotentiality of Some Avian Neural Crest Cells, 355 Nature 161-64 (1988). These results, together with previous observations, therefore suggest that motoneuron differentiation involves a multipotent precursor undergoing progressive stages of commitment.

NEP cells are similar in some respects to, and yet are clearly different from, neuroepithelial cultures from the myelencephalon and telencephalon. M. Murphy et al., Fibroblast Growth Factor Stimulates the Proliferation and Differentiation of Neural Precursor Cell In Vitro, 25 J. Neurosci. Res. 463–75 (1990); J. Drago et al., Fibroblast Growth Factor-Mediated Proliferation of Central Nervous System Precursors Depends on Endogenous Production of Insulin-like Growth Factor 1, 88 Proc. Nat'l Acad. Sci. USA 2199–2203 (1991); T. J. Kilpatrick & B. F. Bartlett, Cloning and Growth of Multipotential Neural Precursors: Requirements for Proliferation and Differentiation, 10 Neuron 255–65 (1993). Like those cells, NEP cells are FGF-dependent, grow as adherent cells, and require an uncharacterized component present in CEE and/or serum. The cells isolated by Murphy et al., Drago et al., and Kilpatrick and Bartlett differ from NEP cells, however, in that they do not form neurospheres. Thus, brain stem and spinal precursor cells appear to be different from cortical precursors. Brain stem neuroepithelial cells are bipotent and have not been shown to differentiate into oligodendrocytes. Further, spinal cord NEP cells rapidly differentiate into astrocytes in the presence of serum. In contrast, brain stem NEP cells remain in an undifferentiated state in the presence of serum.

NEP cells differ from neural crest stem cells in their morphology and antigenic profile. Neural crest cells are more fibroblastic, tend to be migratory, and avoid cell contact. S. Boisseau et al., A Mammalian In Vitro Model to Study Gangliogenesis from Neural Crest Cells, 85 J. Physiol., Paris 117–22 (1991); P. G. Bannerman & D. Pleasure, Protein Growth Factor Requirements of Rat Neural Crest Cells, 36 J. Neurosci. Res. 46–57 (1993). NEP cells appear more flattened and epithelioid and tend to grow as tightly packed monolayers. Unlike rat neural crest cells, NEP cells do not express immunoreactivity for the low affinity neutrophin receptor (p75; Example 4). Moreover, the progeny of NEP cells differ from neural crest cell derivatives in that NEP cells can differentiate into both CNS and PNS cells, whereas neural crest differentiates only into PNS cells. For example, GFAP-immunoreactive cells from NEP cultures do not express detectable nestin and p75 immunoreactivity (Example 6). In contrast, Schwann cells, which are glial cells of the PNS and differentiate from neural crest, express high levels of both p75 and GFAP in culture. D. L. Stemple & D. J. Anderson, Isolation of a Stem Cell for Neurons and Glia from the Mammalian Neural Crest, 71 Cell 973–85 (1992). Schwann cells also express myelin markers such as O4 and P0, D. L. Stemple & D. J. Anderson, supra; M. S. Rao & D. J. Anderson, The Immortalization of a Neural Crest Stem Cell, ASCB 2098 (1994), which are not expressed by GFAP-immunoreactive cells of the CNS derived from NEP cultures (e.g. Example 4). NEP cultures contain A2B5 immunoreactive cells, which subsequently express O4, GalC, and O1 immunoreactivity. Cells with this pattern of antigen expression are not viewed as derivatives of neural crest. Further, while neural-crest-derived parasympathetic neurons express ChAT immunoreactivity in vivo, such neurons have not been described from neural crest cultures. D. J. Anderson, supra. NEP cells, however, readily differentiate to generate large numbers of neurons co-expressing p75 and ChAT. Thus, NEP cells and neural crest stem cells are morphologically and antigenically distinct, generate differentiated progeny that are phenotypically different, and therefore represent different stem cells.

Therefore, the NEP stem cells from the developing spinal cord characterized herein have some properties in common with other nervous system stem cells, but are clearly distinct therefrom. NEP cells represent a stem cell population that undergoes self renewal and differentiates into all major CNS phenotypes in culture, as well as neural crest stem cells and derivatives thereof. NEP cells differ from all previously identified stem cells in their culture conditions and proliferative potential. NEP cell cultures provide a large source of transient cells that can be sorted to obtain differentiated cells types.

The basal medium (NEP medium) used in the experiments described herein comprises DMEM-F12 (GIBCO/BRL, Gaithersburg, Md.) supplemented with 100 $\mu$g/ml transferrin (Calbiochem, San Diego, Calif.), 5, $\mu$g/ml insulin (Sigma Chemical Co., St. Louis, Mo.), 16 $\mu$g/ml putrescine (Sigma), 20 nM progesterone (Sigma), 30 nM selenious acid (Sigma), 1 mg/ml bovine serum albumin (GIBCO/BRL), plus B27 additives (GIBCO/BRL), 25 ng/ml fibroblast growth factor (FGF), and 10% chick embryo extract (CEE). In general, these additives were stored as 100× concentrates at −20° C. until use. Normally, 200 ml of NEP medium was prepared with all additives except CEE and used within two weeks of preparation. CEE was added to the NEP medium at the time of feeding cultured cells.

FGF and CEE were prepared as described in D. L. Stemple & D. J. Anderson, supra; M. S. Rao & D. J. Anderson, supra; L. Sommers et al., Cellular Function of the bHLH Transcription Factor MASH1 in Mammalian Neurogenesis, 15 Neuron 1245–58 (1995), hereby incorporated by reference. FGF is also available commercially (UBI).

Briefly, CEE was prepared as follows. Chick eggs were incubated for 11 days at 38° C. in a humidified atmosphere. Eggs were washed and the embryos were removed and placed in a petri dish containing sterile Minimal Essential Medium (MEM with glutamine and Earle's salts) (GIBCO/BRL) at 4° C. Approximately 10 embryos each were macerated by passage through a 30-mil syringe into a 50-ml test tube. This procedure typically produced about 25 ml of medium. To each 25 ml was added 25 ml of MEM. The tubes were rocked at 4° C. for 1 hour. Sterile hyaluronidase (1 mg/25 g of embryo) (Sigma) was added, and the mixture was centrifuged for 6 hours at 30,000 g. The supernate was collected, passed through a 0.45 $\mu$m filter and then through a 0.22 $\mu$m filter, and stored at −80° C. until use.

Fibronectin (New York Blood Center, New York, N.Y., or Sigma) was diluted to a concentration of 250 $\mu$g/ml in D-PBS (GIBCO/BRL). The fibronectin solution was applied to tissue culture dishes and immediately withdrawn. Collagen (Biomedical Technologies, Inc., Stoughton, Mass.) and poly-L-lysine (Sigma) were each applied to dishes at 20 $\mu$g/ml concentrations. Laminin (GIBCO/BRL or Sigma) was used at a concentration of 50–250 $\mu$g/ml, and dishes were coated overnight. In some cases, dishes were precoated with pDL (30–70 kDa) (Biomedical Technologies, Inc.). The pDL was dissolved in distilled water and applied to tissue culture plates for an hour, and then the excess pDL was withdrawn and the plates were allowed to air dry. Plates were rinsed with water and then allowed to dry again. The pDL-coated plates were then coated with laminin as described above. NEP cells were dissociated and plated on coated dishes, and their development monitored under several different conditions. Fibronectin was chosen as a growth substrate because NEP cells did not adhere to collagen or poly-L-lysine and adhered poorly to laminin. Thus, all subsequent experiments to maintain NEP cells in culture were performed on fibronectin-coated dishes. Laminin-coated dishes were sometimes used, however, to promote differentiation of NEP stem cells.

EXAMPLE 1

The neural tube undergoes closure at embryonic day 10 in rats, Hamburger, supra, and earliest differentiation occurs a day later, Hamburger, supra; Nomes & Das, supra; Altman & Bayer, supra. Embryonic day 10.5 (E10.5) therefore represents the earliest time point when a large number of undifferentiated NEP cells can be easily isolated. Sprague Dawley rat embryos were removed at E10.5 (13–22 somites) and placed in a petri dish containing Ca/Mg-free Hanks balanced salt solution (HBSS, GIBCO/BRL). The trunk segments of the embryos (last 10 somites) were dissected using tungsten needles, rinsed, and then transferred to fresh HBSS. Trunk segments were incubated at 4° C. in 1% trypsin solution (GIBCO/BRL) for a period often to twelve minutes. The trypsin solution was replaced with fresh HBSS containing 10% fetal bovine serum (FBS, GIBCO/BRL). The segments were gently triturated with a Pasteur pipette to release neural tubes free from surrounding somites and connective tissue. Isolated neural tubes were transferred to a 0.05% trypsin/EDTA solution (GIBCO/BRL) for an additional period of ten minutes. Cells were dissociated by trituration and plated at high density in 35 mm fibronectin-coated dishes in NEP medium. Cells were maintained at 37° C. in 5% $CO_2$/95% air. Cells were replated at low density, i.e. $\leq$5000 cells per 35 mm plate, one to three days after plating. Cells from several dishes were then harvested by trypsinization (0.05% trypsin/EDTA solution for two minutes). Cells were then pelleted, resuspended in a small volume, and counted. About 5000 cells were plated in a 35 mm dish (Corning or Nunc). For clonal analysis, cells harvested by trypsinization were plated at a density of 50–100 cells per 35 mm dish. Individual cells were identified and located on the dish by marking the position with a grease pencil. Cells were grown in DMEM/F12 with additives, as described above, for a period ranging from 10–15 days.

EXAMPLE 2

E10.5 rat neural tube cells were dissociated according to the procedure of Example 1 except that the cells were plated at low density and incubated in NEP medium with either acidic FGF (aFGF; 25 ng/ml), basic FGF (bFGF; 25 ng/mil), epidermal growth factor (EGF; 50 ng/ml) or no added factor for 48 hours. Cultured cells were fixed and examined by phase contrast microscopy according to methods well known in the art. Cells grown in aFGF or bFGF survived and increased in density. In contrast, no surviving cells were seen in cultures grown without FGF or with 50 ng/ml EGF. Thus, NEP cells require FGF for survival, and EGF does not support growth of NEP cells in adherent culture.

EXAMPLE 3

In this example, E10.5 rat neural tube cells were dissociated according to the procedure of Example 1, and equal numbers of cells were plated at low density in a 35 mm dish and incubated in NEP medium containing bFGF (25 ng/ml) with 10% CEE or without CEE for 5 days. The cultured cells were then fixed and examined by phase contrast microscopy according to methods well known in the art. In the absence of CEE, cells grew slowly and some cells appeared rounded and phase bright. Cells grown in the presence of 10% CEE appeared more homogeneous and proliferated to form a confluent monolayer. Thus, CEE was required to maintain NEP cells in an undifferentiated state. However, CEE in itself was not a survival factor, and NEP cells did not survive in medium supplemented with CEE in the absence of exogenously added FGF. Thus, CEE contains a component distinct from EGF that, in concert with FGF, maintains NEP cells in an undifferentiated state in culture.

EXAMPLE 4

In this example, NEP cells cultured in FGF and CEE on fibronectin-coated plates for 5 days according to the procedure of Example 3, except for the addition of 5-bromodeoxyuridine (BrdU, 1 $\mu$M concentration, Sigma) at day 2 to some cells, were tested by immunocytochemistry for cell division and differentiation using a variety of antigenic markers. Nestin is a marker for undifferentiated stem cells. U. Lendahl et al., CNS Stem Cells Express a New Class of Intermediate Filament Protein, 60 Cell 585–95 (1990). BrdU incorporation is a marker for determining the number of dividing cells. The antisera used and their concentrations are summarized in Table 1. All secondary antibodies were obtained from Jackson Immunologicals (Westgrove, Pa.) and were used according to the manufacturer's instructions. Staining procedures were carried out as described in D. L. Stemple & D. J. Anderson, supra. Staining for cell surface antigens was carried out in cultures of living cells. For neurofilament proteins, GFAP and $\beta$-III tubulin, cells were fixed with acid-ethanol. For other intracellular antigens, cultures were fixed in 4% formaldehyde for 15 minutes. For BrdU immunocytochemistry, cells were further permeabilized by the procedure of S. P. Memberg & A. K. Hall, Dividing Neuron Precursors Express Neuron-specific Tubulin, 27 Neurobiol. 26–43 (1995), hereby incorporated by reference. Cell cultures were incubated with the selected primary antibody in blocking buffer (PBS, 1 mg/ml bovine serum albumin (BSA), 0.5% triton-X-100, 1% goat serum) for a period of 1 hour, rinsed with PBS, and incubated with a species-specific secondary antibody (Jackson Immunologicals, Westgrove, Pa.) in blocking buffer for an additional hour. Cultures were rinsed with three changes of PBS. Double-labeling and triple-labeling experiments were performed by simultaneously incubating cells in appropriate combinations of primary antibodies followed by non-crossreactive secondary antibodies.

After 5 days in culture, all cells continued to express nestin, but did not express any other marker tested. Moreover, most of the cells had divided and incorporated BrdU over a three-day period. These results indicate that the cells were dividing and were undifferentiated stem cells. NEP cells passaged at a 1:3 dilution every fifth day as adherent cultures could be maintained as nestin-immunoreactive cells that did not express any markers characteristic of differentiated cells over at least three passages. Subsequent passaging over three months maintained nestin-immunoreactive, lineage-negative cells, but in addition, a small percentage of GFAP-immunoreactive cells (1–5%) could be detected. Thus isolated NEP cells, which express nestin immunoreactivity and lack all lineage specific markers for neuronal and glial sublineages, could be passaged and their numbers amplified when grown under non-differentiation conditions.

TABLE 1

| Antibody/Kind | Dilution/Source | Antigen Recognized | Cell type Recognized |
|---|---|---|---|
| Rat 401/mouse IgG | 1:1/DSHB[a] | Intermediate filament | Stem cells, oligo precursors |
| anti-NCAM/ mouse IgG | 1:3/DSHB | Polysialated N-CAM | Neurons |
| anti-$\beta$-III tubulin/ mouse IgG1 | 1:100/Sigma | Intermediate filament | Neurons |
| anti-neurofilament/ mouse IgG2 | 1:100/Sigma | Neurofilament 68 | Neurons |
| anti-ChAT/goat IgG | 1:100/Chemicon[b] | Choline acetyl transferase | Motoneurons |
| anti-glutamate/ rabbit IgG | 1:100/Chemicon | Glutamate | CSN neurons |
| anti-GABA/ rabbit IgG | 1:100/Chemicon | Gamma amino butyric acid | CNS neurons |
| anti-GFAP/ rabbit IgG | 1:500/Accurate | Glial fibrillary acid | Astrocytes |
| anti-A2B5/ mouse IgM | 1:3/BMB[c] | Ganglioside | oligodendrocytes and precursors |
| anti-Gal-C/ mouse IgG | 1:3/BMB | Galactocerebroside | oligodendrocytes and precursors |
| anti-O4/mouse IgM | 1:1/BMB | Sulfatide | oligodendrocytes |
| anti-O1/mouse IgM | 1:3/BMB | Galactocerebroside | oligodendrocytes |

[a]Developmental Studies Hybridoma Bank, Iowa
[b]Chemicon, Temecula, CA
[c]Boehringer Mannheim Biochemicals, Gaithersburg, MD

EXAMPLE 5

The CNS consists of three major phenotypes, neurons, glia, and astrocytes, all of which express characteristic antigenic markers. To determine if undifferentiated, cultured NEP cells could differentiate into CNS neurons and glia, NEP cells grown on fibronectin in NEP medium for 5 days according to the procedure of Example 1 were harvested by trypsinization and replated on laminin-coated plates in neuroepithelial culture medium without the addition of CEE. Omission of CEE was used to promote differentiation. Laminin was used as a substrate instead of fibronectin because laminin has been shown to promote proliferation and neuronal differentiation. J. Drago et al., supra. After 5 days on laminin-coated plates in NEP medium without CEE, the cells were fixed and processed for determining immunoreactivity to β-III tubulin, neurofilament 160 (NF160), low affinity neurotrophin receptor (p75), and choline acetyl transferase (ChAT), according to the procedure of Example 4. Under these conditions, NEP cells rapidly differentiated, as characterized by alterations in morphology and the expression of lineage-specific antigenic markers.

Small phase bright cells with small processes could be seen as early as 48 hours after replating onto laminin-coated plates in the absence of CEE. Cells with this morphology expressed β-III tubulin immunoreactivity, and a subset of the β-III immunoreactive cells also expressed neurofilament 160 (NF160) immunoreactivity. β-III tubulin immunoreactive, NF160-negative cells were also observed, and these cells likely represent immature neurons. S. P. Memberg & A. K. Hall, supra. The number of β-III tubulin immunoreactive cells increased in culture over a period of 5 days, at which time they represented 20%±4% of the total number of cells.

In addition to the small phase bright, β-III tubulin immunoreactive cells, cells with a larger cell soma and more elaborate processes were also seen. These cells were p75, NF160, and ChAT immunoreactive and were observed both as single cells and as clusters. In the developing neural tube, p75 and ChAT immunoreactivity is characteristic of motoneurons. W. Camu & C. E. Henderson, Purification of Embryonic Rat Motoneurons by Panning on a Monoclonal Antibody to the Low-affinity NGF Receptor, 44 J. Neurosci. Meth. 59–70 (1992). The p75, ChAT immunoreactive cells (hereinafter, "motoneurons") represented a small proportion (4%±2%) of the total number of cells.

EXAMPLE 6

In this example, NEP cells grown on fibronectin in NEP medium for 5 days according to the procedure of Example 1 were harvested by trypsinization and replated on fibronectin-coated plates in NEP medium without CEE but with the addition of 10% FBS for a period of 5 days. Omission of CEE was used to promote differentiation. The cells were then fixed and processed for GFAP, p75, nestin, β-III tubulin, and A2B5 immunoreactivity, according to the procedure of Example 4. Under these conditions, NEP cells rapidly differentiated, and the largest proportion of differentiated cells expressed glial fibrillary acid protein (GFAP) immunoreactivity. After 5 days in culture, GFAP immunoreactive cells constituted 73%±6% of the total number of cells present. Two characteristic morphologies could be identified, a flattened, pancake-shaped cell with small or absent processes, and a smaller, more fibroblastic cell with long, elaborate processes. Neither of these two morphologically distinct cells expressed A2B5, p75, or β-III tubulin immunoreactivity, indicating that these cells were most likely type 1 astrocytes. No type 2 astrocytes, as defined by co-expression of A2B5 and GFAP, M. Raff, Glial Cell Diversification in the Rat Optic Nerve, 243 Science 1450–55 (1989); L. E. Lillien & M. C. Raff, Analysis of the Cell-cell Interactions that Control Type-2 Astrocyte Development In Vitro, 4 Neuron 525–34 (1990), were identified, though such type 2 astrocytes have been generated from NEP cells in other culture conditions (e.g. Examples 8 and 12).

EXAMPLE 7

In this example, NEP cells grown on fibronectin in NEP medium for 5 days according to the procedure of Example 1 were harvested by trypsinization and replated on laminin-coated plates in neuroepithelial culture (NEP) medium without the addition of CEE for 5–10 days. Differentiating NEP cells were then labeled, according to the procedure of Example 4, with markers previously identified as being expressed on oligodendrocytes and their precursors: A2B5, GalC, O1, and O4. Three days after replating NEP cells, a subset of the cells began to express A2B5 immunoreactivity. A2B5 immunoreactive cells initially did not express detectable levels of GalC, O4, and O1 immunoreactivity. After an additional three days in culture, however, GalC immunoreactive cells could be seen, which cells also expressed A2B5 immunoreactivity. Such cells appeared flattened and did not have the characteristic morphology of oligodendrocyte-type 2-astrocyte (O-2A) progenitors or mature oligodendrocytes. Longer periods in culture, however, allowed more mature-looking oligodendrocytes with a small body and extensive processes to develop. These cells expressed O1 and GalC immunoreactivity, markers characteristic of differentiated oligodendrocytes. Thus, NEP cells can generate oligodendrocytes that mature over 10 days in culture. The pattern of antigen expression further suggests the existence of a dividing oligodendrocyte precursor that subsequently generates oligodendrocytes, as has been described from spinal cord cultures from older embryos. B. C. Warf et al., supra; R. H. Miller & V. Szigeti, Clonal Analysis of Astrocyte Diversity in Neonatal Spinal Cord Cultures, 115 Development 133–42 (1991).

Therefore, as shown in Examples 5–7, NEP cells grown in culture generate neurons, glia, and oligodendrocytes when replated on laminin in the absence of CEE. This culture condition, while suboptimal for any particular phenotype, is sufficient to generate differentiated progeny and has been used to assess differentiation in subsequent experiments.

EXAMPLE 8

NEP cells grown in culture could be either a homogeneous population of cells where each cell could differentiate into all phenotypes or a heterogeneous population of cells with a variety of differentiation potentials. To distinguish between these possibilities, cultured NEP cells were grown at clonal density, individual cells were circled, and their development followed for a period of 15 days. Clones were analyzed for differentiation by triple labeling using GFAP, β-III tubulin, and A2B5 as markers for astrocytes, neurons, and oligodendrocyte precursors.

For preparation of clonal cultures of neuroepithelial cells, NEP cells prepared according to the procedure of Example 1 were trypsinized and plated in 35 mm dishes coated with fibronectin at a dilution of about 50 cell/dish. In some experiments, however, cells were plated at about 10 cells/dish. Cells were allowed to settle for a period of 4 hours, and then single cells were circled and their development followed in culture. In most experiments, clonal cultures were terminated after 12 days. In experiments to demonstrate oligodendrocyte development, clones were observed for 18–21 days.

For replating individual clones, a glass cloning ring (Fisher Scientific, Pittsburg, Pa.) was placed around each clone and the cells isolated by trypsinization for 1–2 minutes with 100 μl of trypsin/EDTA solution. Cells were resuspended in fresh medium, and an aliquot of cells (50–100 cells) was replated onto fibronectin-coated cultures dishes. Single cells were identified and circled with a grease pencil and their development followed as described above.

Primary or replated clonal culture plates were usually triple labeled with the cell surface antigen and the appropriate secondary antibody being used in live cell culture according to the procedures described in Example 4. Clones were then fixed in 4% paraformaldehyde for 10 minutes and processed sequentially for the other antigens. The diaminobenzidine (DAB, Sigma) reaction to horseradish peroxidase labeled secondary antibodies was always performed after all other staining had been completed because reduced staining with some antigens was observed if the clones were processed for DAB histochemistry first.

At least some clones were stained by all three markers and thus contained all three phenotypes of cells. Thus, at least some NEP cells are capable of generating neurons, astrocytes, and oligodendrocytes. To confirm that A2B5 immunoreactive cells represented oligodendrocytes, some clones were restained with O1or GalC. The results summarized in Table 2 represent 256 colonies from three independent clonal assays.

TABLE 2

| Antigen Expressed | % of Clones |
| --- | --- |
| A2B5 + β-III tubulin | 13 ± 2 |
| A2B5 + GFAP | 28 ± 2 |
| A2B5 + β-III tubulin + GFAP | 42 ± 3 |
| GFAP + β-III tubulin | 17 ± 1 |
| GFAP alone | None |
| β-III tubulin alone | None |
| A2B5 alone | None |

All clones analyzed contained more than one phenotype. Neuron and oligodendrocyte clones, as well as neuron and astrocyte clones were identified. A significant proportion of NEP cells generated colonies containing all three phenotypes of cells. In all cases, when clones were carefully studied, it was possible to identify cells that did not express any of the markers tested, suggesting that precursor cells were still present. Further, no clones that contained only one cell type could be identified, suggesting that at this stage no committed precursors were present in culture.

EXAMPLE 9

To determine if multipotent stem cells underwent self renewal, NEP cells prepared according to the procedure of Example 1 were plated at low density and single cells were observed for 10 days according to the procedure of Example 8. Clones at this stage varied in size from about 100 to several thousand cells. The largest clones were identified, harvested by trypsinization, and a subset of cells was replated on fibronectin-coated plates in NEP medium. Individual cells from each parent clone were circled and observed in culture. Fifteen days after replating, clones were triple labeled for O1β-III tubulin, and GFAP expression. The number of daughter clones that expressed all three markers is shown in Table 3, which contains the pooled results from three independent NEP cell preparations.

TABLE 3

| Clone No. | No. of Cells Observed | No. of Multipotent Daughter Clones |
| --- | --- | --- |
| 1 | 40 | 15 |
| 2 | 34 | 3 |
| 3 | 38 | 12 |
| 4 | 36 | 8 |
| 5 | 42 | 9 |
| 6 | 22 | 2 |
| 7 | 21 | 3 |
| 8 | 13 | 1 |
| 9 | 17 | 8 |
| 10 | 21 | 7 |
| 11 | 19 | 3 |
| 12 | 23 | 4 |
| 13 | 41 | 13 |
| 14 | 16 | 7 |
| 15 | 37 | 9 |

Of the 15 clones that were followed, each contained 1–15 daughter clones (3–50% of replated cells) that had differentiated into neurons, astrocytes, and oligodendrocytes. Thus, all of the clones that were observed generated multipotent daughter cells. Therefore, individual NEP cells are capable of self renewal.

EXAMPLE 10

Stem cells that undergo self renewal and retain their ability to differentiate into multiple phenotypes have been previously described. B. A. Reynolds et al., A Multipotent EGF-responsive Striatal Embryonic Progenitor Cell Produces Neurons and Astrocytes, 12 J. Neurosci. 4565–4574 (1992); B. A. Reynolds et al., Clonal and Population Analysis Demonstrate that an EGF-responsive Mammalian Embryonic CNS Precursor is a Stem Cell, 175 Develop. Biol. 1–13 (1996); A. L. Vescovi et al., bGFG Regulates the Proliferative Fate of Unipotent (Neuronal) and Bipotent (Neuron/Astroglial) EGF-generated CNS Progenitor Cells, 11 Neuron 951–66 (1993); T. J. Kilpatrick & B. F. Bartlett, supra; T. J. Kilpatrick & B. F. Bartlett, Cloned Multipotential Precursors from the Mouse Cerebrum Require FGF-2 whereas Glial Restricted Precursors are Stimulated by either FGF-2 or EGF, 15, J. Neurosci. 3653–61 (1995); A. A. Davis & S. Temple, A Self Renewing Multipotential Stem Cell in Embryonic Rat Cerebral Cortex, 372 Nature 263–66 (1994); S. Temple & A. Davis, Isolated Rat Cortical Progenitor Cells are Maintained in Division In Vitro by Membrane Associated Factors, 120 Development 999–1008 (1994). One such stem cell is the neurosphere isolated from cortical ventricular zone, which can be maintained in an undifferentiated state over multiple passages in defined medium in the presence of EGF. B. A. Reynolds et al. (1992), supra; B. A. Reynolds et al. (1996), supra; A. L. Vescovi et al., supra. To determine if NEP cells could be grown as neurospheres, cells grown in adherent cultures according to the procedure of Example 1 were trypsinized, pelleted, and grown in bacterial plates as suspension cultures at a density of 100–300 cells, i.e. in non-adherent culture at clonal density. The medium used was NEP medium. Most cells did not survive replating, but, on average, 2.5±1.0 cells (1.2%) formed neurospheres. No neurospheres were obtained when cells were grown in NEP medium in which EGF (50 ng/ml) was substituted for FGF (20 ng/ml).

Neurospheres generated in FGF-containing medium were replated onto either fibronectin-coated dishes in non-differentiating medium or onto laminin-coated plates in differentiating medium (NEP medium minus CEE). Spheres grown on fibronectin were labeled with BrdU and nestin, showing that the majority of cells consisted of undifferentiated nestin-immunoreactive, dividing cells. Such undifferentiated cells appeared morphologically similar to NEP cells that were generated from neural tube dissociation, and could be passaged and used to generate additional neurospheres. Spheres grown on laminin were triple labeled for O1, β-III tubulin, and GFAP expression, showing that neurospheres can differentiate into neurons, astrocytes, and oligodendrocytes. Thus, NEP cells and FGF-dependent neurospheres represent identical cells grown under adherent or non-adherent culture conditions, respectively, but are distinct from the EGF-dependent neurospheres generated from older embryos.

EXAMPLE 11

Motoneurons are the earliest cell type to differentiate from caudal neuroepithelium. E.g. Hamburger, supra. N-CAM (neural cell adhesion molecule) and p75 immunoreactive neurons are seen in vivo and in vitro within 12 hours of the time that neural tubes are isolated and NEP cells placed in culture. E. W. Chen & A. Y. Chiu, supra; W. Camu & C. E. Henderson, supra. It is therefore possible that a committed motoneuron precursor was already present at the time NEP cells were placed in culture. To determine if such a precursor existed, NEP clonal cultures were analyzed with motoneuron and other lineage-specific markers. E10.5 NEP cells were isolated and cultured on fibronectin-coated dishes for 5 days, harvested by trypsinization, and replated onto fibronectin-coated 35 mm dishes at clonal density in NEP medium with CEE, according to the procedure of Example 8. Single isolated cells were circled and observed for a period of 10–21 days. Clones were then either (a) double-labeled for ChAT and either β-III tubulin, GFAP, or A2B5, or (b) triple-labeled for ChAT, β-III tubulin, and A2B5 expression, according to the procedure of Example 4. Clones were then scored for the markers they expressed. These results are summarized in Table 4.

TABLE 4

| Antigen Expressed | Proportion of Clones (%) |
|---|---|
| ChAT + β-III tubulin | 26/28 (93%) |
| ChAT + GFAP | 30/32 (94%) |
| ChAT + A2B5 | 24/27 (89%) |

Table 4 represents the data from 87 clones and shows the number of clones expressing both markers when double-labeled. No clones were observed that contained only ChAT immunoreactive cells, thus no clone containing motoneurons alone was observed. Motoneuron containing clones also contained astrocytes, other neurons, and/or oligodendrocytes. These results are evidence, therefore, that there is a common progenitor that can generate motoneurons and other spinal cord cells.

Glial Restricted Precursors Derived from NEP Stem Cells

Multipotent NEP stem cells can be induced to generate self-renewing precursor cells restricted to subsequent glial differentiation. The self-renewing precursor population can be isolated by immunopanning using the monoclonal antibody A2B5 and can be maintained in an undifferentiated state over multiple divisions when grown in platelet derived growth factor (PDGF) and bFGF. A2B5$^+$ cells differ from parental NEP cells in antigenic phenotype and differentiation potential. A2B5$^+$ cells lack the ability to differentiate into neurons under conditions that promote neuronal differentiation in NEP cells. A2B5$^+$ cells retain, however, the ability to differentiate into oligodendrocytes and astrocytes and are thus identified as multipotential glial-restricted precursors.

Figure 2:
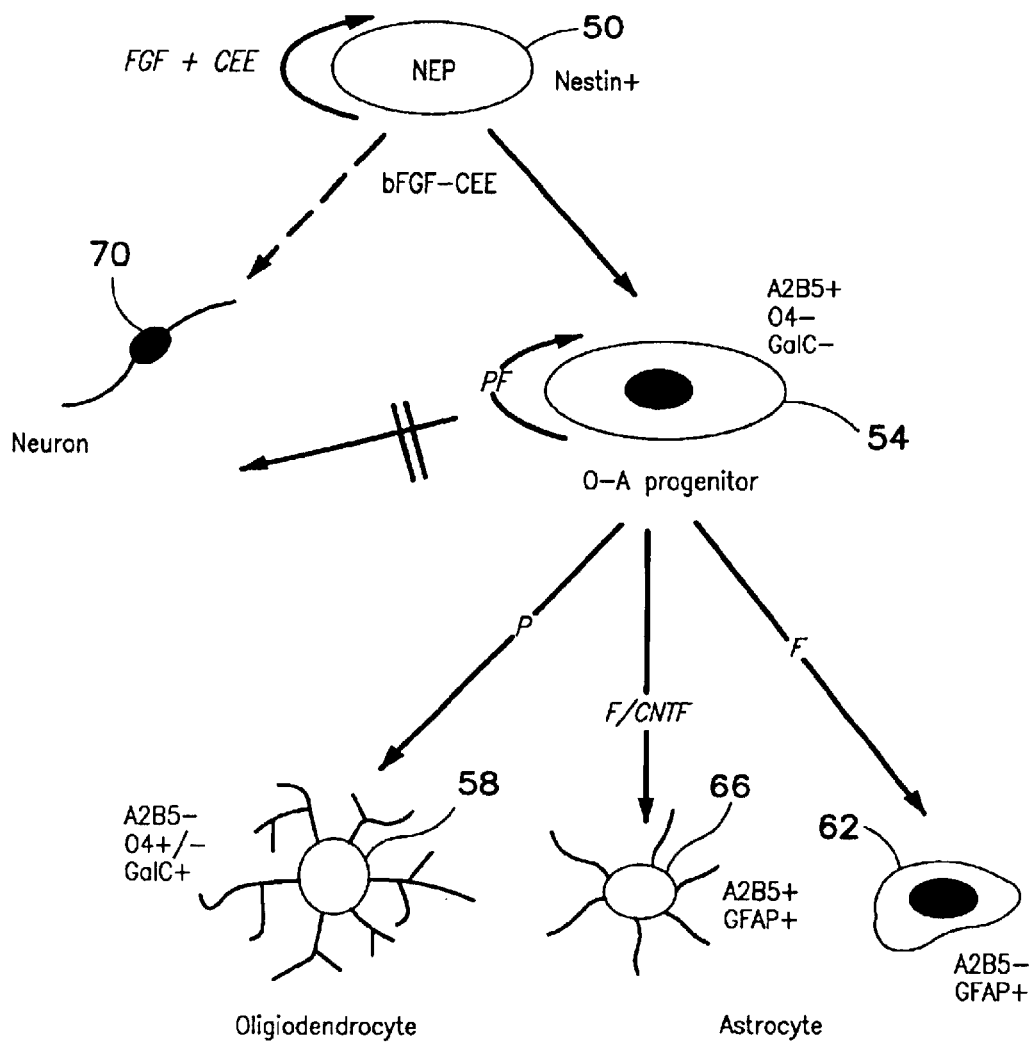
FIG. 2 shows a summary of the immunoreactivities of multipotent NEP stem cells, glial-restricted A2B5$^+$ cells (oligodendrocyte-astrocyte (O-A) progenitor) that arise from NEP cells, and oligodendrocytes and astrocytes that arise from the O-A progenitor.

FIG. 2 shows a model of NEP cell differentiation, wherein multipotent NEP cells 50 have the capability to differentiate into an oligodendrocyte-astrocyte (O-A) progenitor 54 that is capable of self-renewal and also retains the capability to further differentiate into oligodendrocytes 58, type 1 astrocytes 62, and type 2 astrocytes 66. FIG. 2 also illustrates that NEP cells are capable of differentiating into neurons 70, whereas O-A progenitor cells are not.

Several lines of evidence show that A2B5 immunoreactive glial-restricted precursors arise from multipotent NEP cells. First, NEP cells are a homogeneous nestin-positive, A2B5-negative population of cells (Example 4). Second, clonal analysis of NEP cell cultures reveals no clones that give rise to only glial cells (Example 8). Third, A2B5$^+$ cells always arise in clones that contain A2B5$^-$ neurons and astrocytes (Example 8). Thus, there is no evidence that NEP cells contain a committed A2B5$^-$, O-2A progenitor. Rather, a process of differentiation occurs where an NEP cell transits to a more restricted cell type.

The A2B5$^+$ population derived from NEP cells appears homogeneous and uniformly lacks the ability to generate neurons. These A2B5$^+$ cells share some similarities with, but are also different from, other glial restricted precursors identified in the CNS. F. Aloisi et al., Developmental Appearance, Antigenic Profile, and Proliferation of Glial Cells of the Human Embryonic Spinal cord: An Immuno-cytochemical Study Using Dissociated Cultured Cells, 5 Glia 181–81 (1992); H. M. Blau & S. M. Hughes, Cell Lineage in Vertebrate Development, 2 Curr. Biol. 981–85 (1990); R. S. Cameron & P. Rakic, Glial Cell Lineage in Cerebral Cortex: A Review and Synthesis, 4 Glia 124–37 (1991); C. L. Chan et al., Oligodendrocyte-type 2 Astrocyte (O-2A) Progenitor Cells from Neonatal and Adult Rat Optic Nerve Differ in Their Responsiveness to Platelet-Derived Growth Factor, 55 Brain Res. Dev. Brain Res. 275–82 (1990); P. Cochard & M. C. Giess, [Oligodendrocyte Lineage], 189 C R Seances Soc. Biol. Fil. 263–69 (1995); A. A. Davis & S. Temple, supra; G. A. Elder et al., Characterization of Glial Subpopulations in Cultures of the Ovine Central Nervous System, 1 Glia 317–27 (1988); J. Fok-Seang & R. H. Miller, Distribution and Differentiation of A2B5$^+$ Glial Precursors in the Developing Rat Spinal Cord, 37 J. Neurosci. Res. 219—35 (1994); B. P. Fulton et al., Visualization of O-2A Progenitor Cells in Developing and Adult Rat Optic Nerve by Quisqualate-Stimulated Cobalt Uptake, 12 J. Neurosci. 4816–33 (1992); D. S. Galileo et al., Neurons and Glia Arise from a Common Progenitor in Chicken Optic Tectum: Demonstration with Two Retroviruses and Cell Type-Specific Antibodies, 87 Proc. Nat'l Acad. Sci. USA 458–62 (1990); A. L. Gard et al., Oligodendroblasts Distinguished from O-2A Glial Progenitors by Surface Phenotype (O4+GalC−) and Response to Cytokines Using Signal Transducer LIFR Beta, 167 Dev. Biol. 596–608 (1995); R. Hardy & R. Reynolds, Proliferation and Differentiation Potential of Rat Forebrain Oligodendroglial Progenitors Both In Vitro and In Vivo, 111 Development 1061–80 (1991); R. J. Hardy & V. L. Friedrich, Jr., Oligodendrocyte Progenitors Are Generated Throughout the Embryonic Mouse Brain, But Differentiate in Restricted Foci, 122 Development 2059–69 (1996); P. E. Knapp, Studies of Glial Lineages and Proliferation In Vitro Using an Early Marker for Committed Oligodendrocytes, 30 J. Neurosci. Res. 336–45 (1991); M. B. Luskin et al., Neurons, Astrocytes, and Oligodendrocytes of the Rat Cerebral Cortex Originate from Separate Progenitor Cells: An Ultrastructural Analysis of Clonally Related Cells, 13 J. Neurosci. 1730–50 (1993); R. H. Miller, Oligodendrocyte Origins, 19 TINS 92–96 (1996); K. Ono et al., Early Development and Dispersal of Oligodendrocyte Precursors in the Embryonic Chick Spinal Cord, 121 Development 1743–54 (1995); M. C. Raff et al., A Glial Progenitor Cell That Develops In Vitro into an Oligodendrocyte Depending on Culture Medium, 303 Nature 390–96 (1983); M. J. Rivkin et al., Oligodendroglial Development in Human Fetal Cerebrum, 38 Ann. Neurol. 92–101 (1995); P. M. Wood & A. K. Williams, The Generation of Neurons and Oligodendrocytes from a Common Precursor Cell, 7 Neuron 685–93 (1984). NEP-derived A2B5$^+$ cells share several characteristics with optic-nerve-derived O-2A progenitor cells, including morphology, migratory nature, responsiveness to PDGF and bFGF, and the ability to generate oligodendrocytes and type-2 astrocytes. In contrast to postnatal O-2A progenitor cells, however, NEP-derived A2B5$^+$ cells can also give rise to type 1 astrocytes. It thus appears that A2B5$^+$ cells purified from NEP cells represent an earlier stage of glial precursor cell development than the A2B5$^+$ O-2A progenitor cells that have been studied so extensively.

Therefore, the presently described invention provides direct evidence for a lineage relationship between multipotent and lineage-restricted precursor cell populations and identifies morphological, antigenic, and cytokine dependence data to distinguish between the two populations. Moreover, there is established an accessible culture system to follow the development of isolated precursor cells and to study the cellular and molecular events that regulate differentiation processes.

EXAMPLE 12

Neurons, oligodendrocytes, and astrocytes can be identified using a variety of lineage specific markers. G. S. Eisenbarth et al., Monoclonal Antibody to Plasma Membrane Antigen of Neurons, 76 Proc. Nat'l Acad. Sci. USA 4913–17 (1979); E. E. Geisert & A. Frankfurter, The Neuronal Response to Injury As Visualized by Immunostaining of Class β-tubulin in the Rat, 102 Neurosci. Lett. 137–41 (1989); I. Sommer & M. Schachner, Monoclonal Antibody (O1–O4) to Oligodendrocyte Cell Surfaces: An Immunocytological Study in the Central Nervous System, 83 Dev. Biol. 311–27 (1981); P. A. Trimmer et al., Combination of In Situ Hybridization and Immunocytochemistry to Detect Messenger RNAs in Identified CNS Neurons and Glia in Tissue Culture, 39 J. Histochem. Cytochem. 891–98 (1991). Table 5 shows the lineage specific markers used in the present example.

TABLE 5

Antibodies That Identify Specific Cell Types

| Antibody | Antigen | Cell Type |
| --- | --- | --- |
| A2B5 mouse IgM, 1:2 | gangliosides | Glial precursors |
| O4 mouse IgM, 1:2 | galactoside | Oligodendrocytes/precursors |
| α-GalC mouse IgG, 1:2 | galactocerebroside | Oligodendrocytes |
| α-GFAP rabbit IgG, 1:500 | glial fibrillary acid | Astrocytes |
| α-β-III tubulin mouse IgG, 1:400 | intermediate filament | Neurons |
| RT-97 mouse IgG, 1:5 | neurofilament | Neurons |

In addition to defining differentiated cells, some precursor cells can also be recognized by specific antibodies. Two such markers were used herein, nestin and A2B5. Nestin is expressed by a variety of undifferentiated cells in the CNS. E.g., U. Lendahl et al., supra. The A2B5 antibody labels O-2A progenitor cells.

In this example, NEP cells prepared from E10.5 rat neural tube cells according to the procedure of Example 1 were grown in the presence of CEE and bFGF for 3 days and were then replated at 5000 cells/coverslip in NEP medium devoid of CEE for an additional 5 days. Cells were incubated for 24 hours with BrdU and stained with anti-BrdU according to the procedure of Example 4. Parallel cultures were double stained after 7 days with selected combinations of the antibodies described in Table 5. Seventy percent of NEP cells cultured in the absence of CEE for three days exhibited A2B5 immunoreactivity. These A2B5$^+$ cells had a flat morphology and were able to divide in the presence of bFGF. After 4 days in culture in the absence of CEE, 81%±7% of the A2B5$^+$ NEP-derived cells were engaged in cell division as determined by anti-BrdU immunoreactivity. Double labeling of the NEP-derived A2B5$^+$ cells with the antibodies α-nestin, α-GalC, α-GFAP, α-β-III tubulin, and α-p75 (an antibody against the low affinity NGF receptor that recognizes a subset of astrocytes) showed that none of the lineage markers were coexpressed on A2B5$^+$ cells. A substantial subset of the A2B5$^+$ cells, however, expressed α-nestin. This coexpression of α-nestin and A2B5 has been previously described on O-2A progenitor cells. Thus, NEP-derived A2B5-positive cells are antigenically similar to O-2A progenitor cells.

After an additional 2 days in culture, A2B5$^+$ cells had begun to express glial-specific markers. A subpopulation of cells was clearly GalC$^+$ by that time. To confirm that cells were sequentially differentiating into oligodendrocytes, cultures were stained with O4 and α-GalC. As expected, 30% of the O4$^+$ cells coexpressed α-GalC, resembling immature oligodendrocytes. Double labeling with A2B5 and αGFAP showed that 10% of the A2B5$^+$ cells were also GFAP$^+$, resembling the antigenic characteristic of type-2 astrocytes. All the markers that were coexpressed at that later time point on a subset of A2B5$^+$ cells are characteristic of cells belonging to the O-2A lineage. These results suggested that at least a subset of the A2B5$^+$ cells represented glial precursor cells and that A2B5 was a useful marker to define this subpopulation of cells in more detail.

EXAMPLE 13

To determine whether A2B5$^+$ cells arise from multipotent NEP cells or whether A2B5$^+$ cells arise from an already committed subpopulation of A2B5$^-$ NEP cells, NEP cells were plated at clonal densities according to the procedure of Example 8, and their development in culture was followed for 10 days. Cells were then double stained with the antibody combinations A2B5/α-β-III tubulin or A2B5/α-GFAP. The results of analysis of 132 clones are summarized in Table 6.

TABLE 6

| Antigen expressed | % of Clones | No. of Clones |
| --- | --- | --- |
| A2B5$^+$/β-III tubulin$^+$ | 93% | 71/76 |
| A2B5$^+$/GFAP$^+$ | 91% | 51/56 |
| A2B5$^+$ alone | 0 | 0/132 |

Nearly all of the 132 clones consisted of a mixture of A2B5$^+$, GFAP$^+$, and β-III tubulin$^+$ cells. Ninety-one percent of the clones contained cells that were either A2B5$^+$ or GFAP$^+$, while 93% of the clones were either A2B5$^+$ or β-III tubulin$^+$. None of the analyzed clones consisted only of cells that were A2B5$^+$. It is noteworthy that although at this early stage none of the clones contained GalC$^+$ cells, oligodendrocytes could be identified in clonal cultures and in mass culture at later stages (12–15 days after plating on medium devoid of CEE). These clonal analyses suggest that the A2B5$^+$ population arose from a common multipotential A2B5$^-$ precursor cell.

EXAMPLE 14

To determine directly whether NEP-derived A2B5+ cells can only give rise to glial cells, the A2B5+ population was purified by specific antibody capture assay (immunopanning). L. J. Wysocki & V. L. Sato, Panning for Lymphocytes: A Method for Cell Selection, 75 Proc. Nat'l Acad. Sci. 2844–48 (1978); M. Mayer et al., Ciliary Neurotrophic Factor and Leukemia Inhibitory Factor Promote the Generation, Maturation, and Survival of Oligodendrocytes, 120 Development 142–53 (1994), hereby incorporated by reference. Briefly, cells prepared according to Example 1 were trypsinized and the suspension was plated on an A2B5-antibody-coated dish to allow binding of all A2B5+ cells to the plate. The supernate was removed, and the plate was washed with DMEM supplemented with additives (DMEM-BS) described by J. E. Bottenstein & G. H. Sato, Growth of Rat Neuroblastoma Cell Line in Serum-Free Supplemented Medium, 76 Proc. Nat'l Acad. Sci. USA 514–17 (1979), hereby incorporated by reference. The bound cells were scraped off and plated on fibronectin/laminin coated glass coverslips in 300 $\mu$l DMEM-BS±growth factors at 5000 cells/well. In the final culture, the contaminating A2B5− cells represented less than 10% of the total cells. The A2B5 antibody for coating the plates was used at a concentration of 5 $\mu$g/ml protein. Cells were allowed to bind to the plate for 20–30 minutes in a 37° C. incubator. Growth factors were added every other day at a concentration of 10 ng/ml. Recombinant human PDGF-AA was obtained from Chiron Corporation. Recombinant rat ciliary neurotrophic factor (CNTF) was obtained from Precision Research Biochemicals. Recombinant bFGF was purchased from PeroTech Inc., and retinoic acid (RA) was from Sigma.

After 5 days of culturing NEP cells in the absence of CEE, cells were immunopurified, plated on fibronectin/laminin coated dishes, and exposed to cytokines previously associated with differentiation of precursor into oligodendrocytes, astrocytes, or neurons. The A2B5-panned population was >98% positive for A2B5+ cells when stained one hour after panning. Staining 24 hours after plating showed that all cells of the panned population were A2B5+ and did not express any other lineage markers tested.

Panned cultures in the presence of bFGF and no other growth factors for 5 days consisted of 1% oligodendrocytes, 50% GFAP+ astrocytes, and 49% A2B5+ cells. The proportion of differentiated cells was significantly shifted when the bFGF-containing medium was replaced after 3 days with medium supplemented only with PDGF. Under these conditions, the culture consisted of 30% oligodendrocytes, 50% astrocytes, and 20% A2B5+ cells.

Although growth in the presence of bFGF alone was sufficient to allow differentiation of NEP cells into neurons in the parent population, no neurons were detected in the A2B5+ panned population cultured in the presence of bFGF. To enhance the probability of neuronal differentiation, the medium was additionally supplemented with retinoic acid, which significantly increased neuronal differentiation in the parent NEP cell population. Even in this neuron-promoting environment, the immunopurified A2B5+ population did not contain $\beta$-III tubulin+ cells. It was unlikely that the neuronal population was lost through selective cell death, because no significant cell death was observed in the panned mass cultures at any time, suggesting that neurons did not appear rapidly and die. Moreover, no evidence of $\beta$-III tubulin+ ghosts was detected.

These results suggest that the precursor cells that are responsible for generating neurons were not part of the immunopurified A2B5+ population. As the A2B5-panned cells gave rise to astrocytes and oligodendrocytes, but not to neurons, it appeared that the A2B5+ population contained precursor cells that were restricted to glial lineage.

EXAMPLE 15

Mass culture experiments suggested that the A2B5-panned population prepared according to Example 14 contained cells with a differentiation potential restricted to glial lineages. This experiment, however, did not address whether astrocytes and oligodendrocytes are generated from committed unipotential cells present in the A2B5+ population or whether single cells are bipotential and can generate both astrocytes and oligodendrocytes. To address this question, clonal experiments were performed, wherein the A2B5-panned population was stained with A2B5 1 day after panning, and cells were plated at limiting dilution in 96-well plates. Wells were scored with immunofluorescence, and wells with one A2B5+ stained cell were recorded and cultured in PDGF/bFGF for 7 days. This procedure allowed the expansion of clones and also minimized the amount of cell death occurring when single cells were directly plated into differentiation conditions. After 7 days, expanded clones contained from 50–200 cells and were uniformly A2B5+.

The majority of the clones (51) were first washed with bFGF-free DMEM-BS and then switched to PDGF-supplemented medium, an effective culture condition to induce oligodendrocyte generation, as shown in mass culture experiments. All clones contained oligodendrocytes, GFAP+ astrocytes, and A2B5+ cells, while none of the clones contained $\beta$-III tubulin+ cells, suggesting that single A2B5+ cells were at least bipotential and also were restricted to glial cell lineages (Table 7).

TABLE 7

| | Growth Condition | |
|---|---|---|
| Marker expressed | PDGF | FGF/CNTF |
| A2B5+/GFAP+ | 0 | 6 |
| A2B5+ | 51 | 6 |
| GFAP+ | 51 | 4 |
| GalC+ | 51 | 1 |
| $\beta$-III tubulin+ | 0 | 0 |
| Total No. of Clones | 51 | 6 |

The differentiation potential of A2B5+ cells in a culture medium supplemented with bFGF and CNTF was also tested. From the panned mass culture experiments it seemed clear that bFGF alone leads to an increase in the number of GFAP+ astrocytes and a decrease in the number of oligodendrocytes. Depending on culture conditions, CNTF has been shown to promote oligodendrocyte generation, M. Mayer et al., supra, or to lead to the generation of type-2 astrocytes, which are GFAP+ and transiently express A2B5. L. E. Lillien & M. C. Raff, Differentiation Signals in the CNS: Type-2 Astrocyte Development In Vitro as a Model System, 5 Neuron 5896–6273 (1990). Six clones were analyzed that were expanded in PDGF/bFGF and then switched to bFGF/CNTF. Surprisingly, all six clones contained cells that were A2B5+/GFAP+, resembling the type-2 astrocyte phenotype. Only 1 clone contained GalC+ oligodendrocytes, and no clone contained $\beta$-III tubulin+ cells. This result suggested that in the presence of CNTF and bFGF, A2B5+ cells predominantly differentiate into cells with a type-2 astrocyte phenotype.

Five A2B5+ clone were analyzed in different neuron-promoting conditions and, as before, were unable to generate neurons. Five PDGF/bFGF expanded clones were trypsinized, divided into two portions and replated into either bFGF alone or bFGF supplemented with retinoic acid. Clones were stained with the antibodies A2B5, α-GFAP, α-GalC, and α-β-III tubulin (Table 8).

TABLE 8

| Marker expressed | Growth Condition | |
|---|---|---|
| | FGF | FGF/RA |
| A2B5+/GFAP+ | 0 | 0 |
| A2B5+ | 5 | 5 |
| GFAP+ | 5 | 5 |
| GalC+ | 1 | 0 |
| β-III tubulin+ | 0 | 0 |
| Total No. of Clones | 5 | 5 |

None of the clones, regardless of whether cells were grown in bFGF alone or bFGF/RA, contained β-III tubulin immunoreactivity. In contrast, all five clones consisted of a mixture of cells that were either A2B5+ or GFAP+, but not both. Only one clone grown in bFGF alone contained GalC immunoreactive oligodendrocytes, whereas in bFGF/RA, no GalC+ oligodendrocytes were found. These data support the initial observation, that A2B5+ cells isolated from induced NEP cell cultures were multipotential and restricted in their differentiation potential to cells of the glial lineages.

EXAMPLE 16

To fulfill the criteria of a true intermediate precursor, cells need to have an extended self-renewal capacity without losing the ability to differentiate into more than one specific cell type. To test the self-renewal capacity of individual A2B5+ cells, two clones expanded in PDGF/bFGF for 7 days were selected for long-term culture and passaging. The two clones were refed every other day with PDGF/bFGF and maintained for a total of 3 months with 4 serial passages. Clones were grown in PDGF/bFGF, as this combination of cytokines apparently inhibited differentiation and promoted division. Cells were stained before and after each passage and were negative for all differentiation markers tested, except for A2B5+, at all time points.

To determine the differentiation potential of long term clones, during each passage single cells were replated, re-expanded to 50–200 cells, and switched to PDGF alone to promote differentiation. In these secondary cultures, oligodendrocytes and astrocytes appeared consistently after 8–10 days. The ability to differentiate into oligodendrocytes and astrocytes was not altered significantly with increased passages, suggesting that these long-term propagated cells were still multipotential.

These results show that A2B5+ cells that differentiate from multipotent NEP cells can be expanded and propagated as precursor cells. Passaged individual A2B5+ cells self renew and are able to generate oligodendrocytes, A2B5+ and A2B5− astrocytes, but not neurons. NEP-derived A2B5+ cells thus represent multipotential intermediate precursor cells restricted to glial lineages.

Neural Crest Stem Cells Derived from NEP Stem Cells

Neural crest stem cells (NCSC's) are a transient population of cells that arise at or around the time of neural tube closure, undergo extensive migration, and generate a prodigious array of phenotypes. N. M. Le Douarin, The Neural Crest (Cambridge Univ. Press, 1982); M. Bronner-Fraser, Origins and Developmental Potential of the Neural Crest, 218 Exp. Cell Res. 405–417 (1995); M. Bronner-Fraser, Origin of the Avian Neural Crest, 13 Stem Cells (Dayt). 640–646 (1995). Differentiation likely occurs through a series of progressive restrictions in developmental fates. D. J. Anderson, The Neural Crest Lineage Problem: Neuropoiesis?, 3 Neuron 1–12 (1989); D. J. Anderson, Cell and Molecular Biology of Neural Crest Cell Lineage Diversification, 3 Curr. Opin. Neurobiol. 8–13 (1993). Like neurospheres and NEP cells, NCSC's are multipotent and show at least limited self renewal capacity. NCSC's, therefore, represent a stem cell for the peripheral nervous system.

NCSC's can be distinguished from CNS stem cells by their morphology, expression of low affinity nerve growth factor NGF) receptor (in rodent crest), by the progeny they generate, and by their inability to generate CNS derivatives as described above. NSCS's differentiate into Schwann cells, sensory, sympathetic, and enteric neurons, as well as non-neural derivatives, such as cartilage, bone, melanocytes, and smooth muscle (derivatives not reported from CNS stem cells). Mature, NCSC-derived cells express phenotypic markers that can be used to distinguish them from related cells in the CNS. For example, Schwann cells can be distinguished from astrocytes and oligodendrocytes by the co-expression of GFAP and myelination antigens such as GalC, P0, O4, and the like. Peripherin and tyrosine hydroxylate (TH) expression is characteristic of sympathetic neurons of the PNS, but is generally seen only in limited populations of CNS derivatives. Cells expressing markers characteristic of NCSC derivatives have not been shown to arise from either neurospheres of NEP cells. Further, although NCSC's are multipotent stem cells of the PNS, they seem incapable of generating CNS derivatives, and transplantation of primary crest cells and cell lines in to the CNS results in Schwann cell differentiation. Thus, CNS stem cells and NCSC's represent two different kinds of stem cells.

The lineage relationship between CNS stem cells and NCSC's has not heretofore been closely analyzed in rodents. Either two independent lineages have segregated at the time of neural tube closure or the two populations are lineally related. Evidence suggesting both possibilities exists from experiments analyzing avian crest development. Several studies have shown that not only have crest cells segregated prior to neural tube closure, but that the crest population has already been segregated into subtypes that have a limited differentiation potential. For example, early and late migrating crest cells have been described that differ in their ability to generate melanocytes and sensory neurons. J. A. Weston, The Sequential Segregation and Fate of Developmentally-restricted Intermediate Cell Populations in the Neural Crest Lineage, 25 Curr. Topics Dev. Biol. 133–153 (1991); P. Henion & J. Weston, Timing and Pattern of Cell Fate Restrictions in the Neural Crest Lineage, 124 Development 4351–4359 (1997). Other experiments, J. D. Moury & A. G. Jacobson, Neural Fold Formation at Newly Created Boundaries between Neural Plate and Epidermis in the Axolotl, 133 Dev. Biol. 243–253 (1989); M. A. Selleck & M. Bronner-Fraser, Origins of the Avian Neural Crest: The Role of Neural Plate-Epidermal Interactions, 121 Development 525–538 (1995), have shown that at least some neural crest cells arise from the ectoderm in juxtaposition with the neural folds rather than from neural plate cells that form the neural tube. Neural tube rotation experiments performed at a later stage in development, J. A. Weston, A Radiographic Analysis of the Migration and Localization of Trunk Neural Crest in the Chick, 6 Dev. Biol. 279–310 (1963); C. D. Stern et al., Tissue Interactions Affecting the Migration and Differentiation of Neural Crest Cells in the Chick Embryo, 113 Development 207–216 (1991), show that when the ventral neural tube is placed dorsally it will not generate neural crest. Rather, neural crest will arise ventrally from the rotated dorsal tube, suggesting that cells have become committed to CNS or PNS fates as early as stage 15.

Other experiments analyzing crest development in chicks and quails have suggested that segregation is not absolute. Single cell labeling experiments have identified precursors whose progeny have populated both the CNS and the periphery. J. R. Sanes, Analysing Cell Lineage with a Recombinant Retrovirus, 12 TINS 21–28 (1989); S. M. Leber et al., Lineage, Arrangement, and Death of Clonally Related Motoneurons in Chick Spinal Cord, 10 J. Neurosci. 2451–2462 (1990); M. Bronner-Fraser & S. E. Fraser, 355 Nature 161–164 (1988), supra; M. Bronner-Fraser & S. E. Fraser, Developmental Potentials of Avian Trunk Neural Crest Cells In Situ, 3 Neuron 755–766 (1989); K. B. Artinger et al., Dorsal and Ventral Types Can Arise from Common Neural Tube Progenitors, 172 Dev. Biol. 591–601 (1995). Morphological analysis has indicated that cells have also adopted appropriate PNS fates. These experiments strongly suggested that a common CNS-PNS progenitor exists in vivo. Neural tube ablation experiments has also suggested that neuroepithelial cells present in the developing neural tube have not lost their ability to generate PNS derivatives. If the neural tube is ablated up to 6 hours after normal crest migration, the ventral neural tube cells that do not normally generate neural crest will readily generate migratory cells that will populate appropriate PNS ganglia. T. Scherson et al., Regulative Capacity of the Cranial Neural Tube to Form Neural Crest, 118 Development 1049–1062 (1993). These studies, in contrast to the studies cited above, suggest that a common progenitor does exist at some early stage in development (even after neural tube closure), and that this progenitor generates both CNS and PNS derivatives in vivo.

Corresponding experiments demonstrating a common CNS-PNS precursor have not been performed in rodents, and the issue of whether such a common precursor exists remains open. Further, most fo the results from chick embryos suggest that if a common CNS-PNS precursor exists, its proliferative potential is rapidly lost soon after crest has migrated, suggesting that the CNS stem cells isolated in rodents may not have the ability to generate crest-like cells. Indeed, little evidence exists to show that the developing rodent neural tube can generate neural crest after neural tube closure in rodents. Indeed, even in neural tubes isolated at E10.5 (a time of normal crest outgrowth) and placed in culture, neural crest outgrowth occurs only from the dorsal surface. This raises the possibility that neural crest and CNS stem cell lineages have segregated as early as E11. However, alternative explanations, such as the lack of an appropriate signal in explant cultures, cannot be excluded.

To test the lineage relationship between CNS and PNS, the differentiation properties of NEP stem cells have been examined. Evidence is presented herein that individual NEP cells can generate PNS derivatives in both mass and clonal culture. It is shown that differentiation into PNS derivatives likely involves the generation of neural crest stem cells. These date suggest a transition from one stem cell to another stem cell of a more restricted developmental potential.

EXAMPLE 17

NEP Cells Can Generate Schwann Cells and Smooth Muscle

To determine if NEP cells can differentiate into neural crest-derived PNS cells, two types of crest cell derivatives were examined, Schwann cells and smooth muscle cells. Schwann cells can be distinguished from astrocytes by their co-expression of GFAP, the low affinity NGF receptor, as well as myelination antigens. D. L. Stemple & D. J. Anderson, 71 Cell 973–985 (1992), supra; N. M. Shah et al., Alternative Neural Crest Cell Fates Are Instructively Promoted by TGFbeta Superfamily Members, 85 Cell 331–343 (1996); N. M. Shah & D. J. Anderson, Integration of Multiple Instructive Cues by Neural Crest Stem Cells Reveals Cell-intrinsic Biases in Relative Growth Factor Responsiveness, 94 Proc. Nat'l Acad. Sci. USA 11369–11374 (1997); R. Mirsky et al., Development and Differentiation of Schwann Cells, 152 Rev. Neurol. (Paris) 308–313 (1996). Smooth muscle can be identified by the expression of smooth muscle specific actin (SMA) and the co-expression of desmin. N. M. Shah et al., supra; N. M. Shah & D. J. Anderson, supra.

E10-5 NEP cells prepared according to the procedure of Example 1 were grown on fibronectin for 5 days and then were harvested by trypsinization and replated onto fibronectin coated 35 mm dishes in neural crest medium with CEE. D. L. Stemple & D. J. Anderson, 71 Cell 973–985 (1992), supra. In brief, neural crest medium was prepared by supplementing DMEM/F12 medium with the additives described by J. E. Bottenstein & G. H. Sato, 76 Proc. Nat'l Acad. Sci. USA 514–17 (1979), supra, 10% CEE, 50 ng/ml NGF (UBI), 10 ng/ml FGF (UBI), and 100 ng/ml EGF (UBI). Immunohistochemistry was carried out according to the procedure of Example 4. Antibodies not mentioned in Table 1 were obtained from the Developmental Studies Hybridoma Bank at the University of Iowa.

One dish was stained with nestin and p75 one day after plating, which showed that dissociated NEP cells do not express p75 (the low affinity neurotrophin receptor) immunoreactivity. No p75 immunoreactivity was detected.

P75 immunonegative NEP cells were grown in differentiation conditions (neural crest medium with CEE) to promote crest cell differentiation, then maintained in the neural crest medium for 10–15 days, and the presence of smooth muscle cells and Schwann cells was analyzed by immunohistochemistry. Cells were allowed to differentiate for 5 days or for 10 days. Cells cultured for 5 days were stained for DAPI/p75, while cells cultured for 10 days were double-labeled for SMA and nestin, or p75 and GFAP. Significant numbers of Schwann cells ($p75^+$, $GFAP^+$) and smooth muscle cells ($p75^-$, $SMA^+$) were present, indicating that both of these PNS derivatives could be generated from p75-immunonegative NEP cells.

EXAMPLE 18

NEP Cells Generate Neural Crest Cells in Culture

In this example, NEP cells grown on fibronectin for 5 days were harvested by trypsinization and replated onto fibronectin coated 35 mm dishes in neural crest medium with CEE. Cells were allowed to differentiate for 5 days and were then double-labeled for p75 and nestin expression, E-NCAM, A2B5, and GFAP. Schwann and smooth muscle cells were generated according to this procedure. These PNS derivatives were invariably preceded by the presence of p75-immunoreactive cells. Two distinct types of p75 immunoreactive cells could be distinguished. First, neuronal appearing cells that were phase bright and had large cell bodies and long processes were observed. These cells were likely motoneurons, since double-labeling showed that most p75-immunoreactive neuronal cells co-expressed choline-acetyl-transferase (ChAT) immunoreactivity. Second, a more flat fibroblastic appearing cell was present. These cells occurred in clusters. Double-labeling of these cells showed that they were nestin immunoreactive, did not express lineage markers such as GFAP and E-NCAM, and did not label with the A2B5 monoclonal antibody. The absence of lineage markers and the co-expression of p75 and nestin have been considered hallmarks of neural crest in rodents. D. L. Stemple & D. J. Anderson, supra. Thus, p75-immunonegative NEP cells could generate p75-immunoreactive crest-like cells as well as NCSC derivatives.

EXAMPLE 19
NEP-Derived p75 Immunoreactive Cells Generate Neural Crest-Derived Cells in Mass Culture To further determine if NEP-derived p75-immunoreactive cells have the ability to differentiate into NCSC derivatives, NEP cells were allowed to differentiate in culture by replating on laminin coated dishes and withdrawing CEE. P75-positive cells were selected by immunopanning according to the procedure of Example 14, except that anti-p75 antibody was used for selecting cells, and plated in neural crest differentiation medium.

In brief, immunopanning was carried out by trypsinizing cells and plating the resulting suspension on a p75 antibody coated dish to allow binding of all p75$^+$ cells to the plate. P75$^+$ dishes were prepared by sequentially coating tissue culture dishes with an unlabeled anti-nouse IgG antibody overnight, rinsing dishes with DPBS, and coating with p75 antibody (IgG192, Developmental Studies Hybridoma Bank, University of Iowa) for 1 hour at room temperature. Cells were allowed to bind for one hour at room temperature. Unbound cells were removed and the plate was washed with DMEM supplemented with additives described by Bottenstein & Sato, supra (DMEM-BS). Bound cells were scraped off and plated on fibronectin/laminin coated dishes in 1 ml of DMEM-BS±growth factors in either mass (5000 cells/dish) or clonal culture (100 cells/dish). Growth factors were added every other day. In all cases, an aliquot of cells was analyzed the next day to determine the efficiency of the immunopanning. In general, greater than 90% of the bound cells expressed detectable p75 immunoreactivity.

To promote maturation of Schwann cells, differentiated p75-immunoreactive cells obtained by immunopanning were grown in neural crest medium with the addition of dibutyl cyclic AMP (5 $\mu$M, Sigma) for an additional 7 days. To promote smooth muscle differentiation, crest cells were grown in neural crest medium supplemented with 10% fetal bovine serum (Hyclone Labs, Logan, Utah). After 7 or 15 days, the expression of differentiation markers was assayed. P75-positive cells differentiated into β-III tubulin- and GFAP-immunoreactive cells. The GFAP-immunoreactive cells expressed p75, and a subset of the cells expressed O4, a myelination specific antigen. This pattern of antigen expression is characteristic of Schwann cells. D. L. Stemple & D. J. Anderson, supra; M. Rao & D. J. Anderson, The Immortalization of a Neural Crest Stem Cell, 7 J. Neurobio. 722–46 (1996); R. Mirsky et al., supra. Neurons that differentiated expressed peripherin, and a subset of the cells expressed TH and MASH, markers characteristic of sympathetic and enteric neurons. This pattern of differentiation into peripherin-immunoreactive neurons is similar to neural crest differentiation under identical culture conditions. L. Sommers et al., supra; M. Rao & D. J. Anderson, supra. Thus, p75-immunoreactive cells isolated from NEP cells were morphologically and phenotypically identical to neural crest and responded in culture in a similar fashion. P75-immunoreactive cells did not generate oligodendrocytes, as characterized by GalC and O4 immunoreactivity, in all culture conditions tested. In contrast, NEP precursor cells readily differentiated into oligodendrocytes in culture, as described above. Thus, NEP-derived p75-immunoreactive cells generated PNS derivatives (peripheral neurons, smooth muscle, and Schwann cells) but not CNS derivatives.

EXAMPLE 20
NEP-Derived p75-Immunoreactive Cells Grow in Clonal Culture to Generate Neurons, Smooth Muscle, and Schwann Cells To determine if individual NEP-derived, p75-immunoreactive cells were multipotent, the differentiation potential of such cells grown in clonal culture was examined. Thus, NEP cells from E10.5 embryos were isolated, induced to differentiate by the addition of RA and withdrawal of FGF and the addition of 5 ng/ml of BMP-2. P75-immunoreactive cells were isolated by immunopanning and plated in clonal culture, and the differentiation of individual clones was followed by expression of antigen markers. NEP-derived p75$^+$ cells were grown in neural crest medium.

Both spontaneously differentiating p75-immunoreactive cells as well as BMP-2-induced p75-immunoreactive cells were tested with identical results. BMP-2-induced p75-immunoreactive cells were plated at clonal density and colonies were assessed after 10 days in culture. Clonal analysis indicated that most clones (14/17) derived from p75-immunoreative cells were multipotential and that a significant proportion of the clones contained more than one kind of differentiated cell. Both neuron and smooth muscle containing as well as glial and smooth muscle containing clones could be identified. Tripotential clones were rare (2/17). Only one unipotential clone, which consisted of primarily smooth muscle cells, was identified. Thus, most NEP-derived (or BMP-2-induced) p75-positive cells are at least bipotent and can differentiate into neural and non-neural derivatives.

EXAMPLE 21
NEP Cells Form Colonies Containing A2B5- and p75-Immunoreactive Cells The results presented above suggest that NEP cells can generate both CNS and PNS derivatives. It was possible, however, that NEP cultures contained two distinct populations of cells indistinguishable by available antigens, one of which generates CNS cells and the other, PNS cells. To distinguish between these possibilities, the ability of individual NEP cells to generate CNS and PNS precursor cells was examined. P75 was selected as a marker for neural crest, and A2B5 as a marker for oligodendrocyte precursors. P75 was used because it is expressed by crest cells, and by double-labeling with neuronal markers, other populations (such as motoneurons) that may express this marker could be excluded. A2B5 was used as a glial marker, since it has previously been shown that A2B5 recognizes a a glial precursor in rat neuroepithelial cell cultures. U.S. Ser. No. 08/980,850; M. Rao et al., A Novel Tripotential Glial Precursor Cell Is Present in the Developing Spinal Cord, Proc. Nat'l Acad. Sci. USA, (in the press); M. Rao & M. Mayer-Proschel, Neuroepithelial Cells from Embryonic Spinal Cord Can Give Rise to Glial Precursors, 188 Dev. Biol. 48–63 (1997). This combination of p75 and A2B5, therefore, allowed detection of both CNS and PNS derivatives without necessitating the use of multiple antibodies.

E10.5 NEP cells grown on fibronectin for 5 days were harvested by trypsinization and replated onto fibronectin-coated 35 mm dishes at clonal density (50–100 cells/35 mm dish) in NEP medium. Single isolated cells were circled and followed for 15 days.

Clonal analysis showed that individual NEP cells could generate both A2B5 and p75-immunoreactive cells. Double labeling showed that p75 and A2B5 were expressed in non-overlapping populations of cells and that the percentage of p75-immunoreactive cells in a clone varied from 5–50%. No clone consisting of only p75-immunoreactive cells or only A2B5-immunoreactive cells was seen. In all cases, unlabeled cells were also present, as shown in Table 9.

TABLE 9

| Antigen Expressed | No. of Clones (%) |
| --- | --- |
| p75$^+$, A2B5$^-$, and unlabeled cells | 15 (23.8%) |
| P75$^-$, A2B5$^+$, and unlabeled cells | 17 (26.9%) |
| p75$^+$, A2B5$^+$, and unlabeled cells | 31 (49.2%) |
| Total No. of Clones | 63 (100%) |

EXAMPLE 22
NEP Cells Form Colonies Containing Both CNS and PNS Derivatives

To further confirm the presence of both CNS and PNS derivatives in the same clone, a subset of NEP clones was allowed to mature further, and the co-expression of SMA with A2B5 and β-III tubulin was analyzed. A2B5 was chosen, because it was previously demonstrated that A2B5-immunoreactivity identifies a CNS glial precursor. M. Rao & M. Mayer-Proschel, supra. Thus, E10.5 NEP cells were grown on fibronectin for 5 days, harvested by trypsinization, and replated onto fibronectin-coated dishes at clonal density (50–100 cells/35 mm dish) in NEP medium with CEE. Single isolated cells were circled and followed for 15 days.

Clones containing A2B5- and SMA-immunoreactive cells, as well as clones containing β-III tubulin and SMA were present. Approximately 40% of the clones showed the presence of both A2B5 and SMA-immunoreactive cells, suggesting that both CNA and PNS derivatives were present in the same culture.

EXAMPLE 23
BMP-2 Regulates the Number of p75-Immunoreactive Cells Present in Culture It has previously been suggested that dorsalizing signals may regulate the differentiation of precursor cells into CNS or PNS stem cells. M. E. Dickinson et al., Dorsalization of the Neural Tube by the Non-neural Ectoderm, 121 Development 2099–2106 (1995); K. F. Liem, Jr. et al., Dorsal Differentiation of Neural Plate Cells Induced by BMP-mediated Signals from Epidermal Ectoderm, 82 Cell 969–979 (1995). To determine if dorsalizing signals such as BMP could promote NEP cell differentiation into p75-immunoreactive crest cells, the effect of BMP-2 was examined.

E10.5 NEP cells were grown on fibronectin for 5 days, harvested by trypsinization, and replated onto fibronectin-coated 35 mm dishes in neural crest medium with CEE and either with 10 ng/ml of BMP-2 or with 100 ng/ml of shh. Cells were allowed to differentiate for two additional days and then were double-labeled for DAPI immunohistochemistry or for p75-immunoreactivity.

Ten ng/ml of BMP-2 caused a large increase (four-fold) in the number of p75-immunoreactive cells as well as in the intensity of p75-immunoreactivity. Both neuronal and non-neuronal p75 immunoreactive cells were detectable. P75-immunoreactive cells that did not appear neuronal in morphology and did not express detectable β-III tubulin (a neuronal marker), and A2B5- or GFAP-immunoreactive cells were considered to be neural crest cells. The identity of crest cells was confirmed by analyzing the differential potential of immunopanned cells.

EXAMPLE 24
BMP-2 Acts as an Instructive Molecule to Regulate Neural Crest Differentiation To determine if BMP promoted crest differentiation by increasing proliferation, the effect of BMP on NEP cells mitosis was examined by BRDU incorporation. E10.5 NEP cells grown on fibronectin for 5 days were harvested by trypsinization and replated onto fibronectin-coated 35 mm dishes with or without the addition of 10 ng/ml of BMP-2. Cells were allowed to differentiate for two additional days and then double-labeled for BRDU and DAPI immunohistochemistry.

Figure 3:
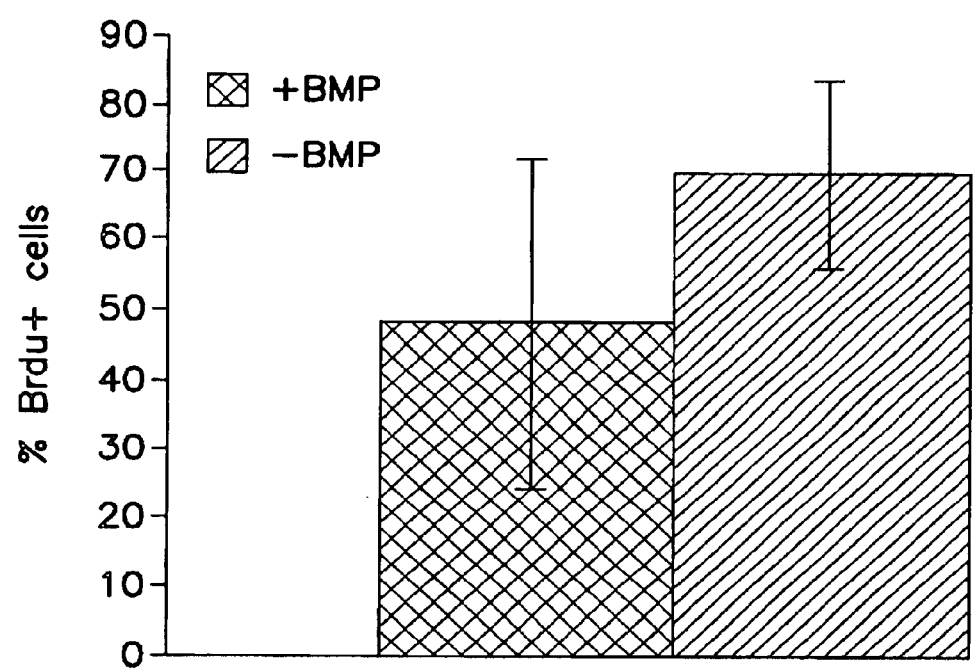
FIG. 3 shows a graphical representation of the percentage of NEP cells undergoing division in the presence or absence of BMP.

BMP appeared to inhibit overall mitosis. BMP did not selectively promote mitosis of p75-immunoreactive cells, suggesting that cells did not need to undergo cell division to determine phenotype. This was assessed directly by plating NEP cells at low density and determining if p75-immunoreactivity could be acquired without undergoing cell division. Thus, BMP can act as an instructive molecule to bias cells to differentiate into p75-immunoreactive crest-like cells, indicating that the choice to become a CNS stem cell or a NCSC can be regulated by extrinsic signals. FIG. 3 summarizes the results from counting random fields from two independent experiments. The difference is statistically significant at the 95% confidence limit using the student T-test.

These results demonstrate the existence of a common CNS-PNS precursor that, in addition to generating neurons, astrocytes, and oligodendrocytes of the CNS, can also generate Schwann cells and smooth muscle in mass and clonal culture. Differentiation into smooth muscle and Schwann cells is preceded by the generation of a p75-immunoreactive stem cell that is morphologically and phenotypically identical to the previously characterized NCSC. NEP-derived NCSCs are self-renewing multipotent cells that can generate both neural and non-neural derivatives. These results show that the choice of differentiating into CNS or PNS stem cells can be regulated in vitro by BMP-2 and that BMP-2 regulates crest differentiation without stimulating mitosis. Individual cells can differentiate from NEP to crest without undergoing cell division, suggesting that BMP acts as an instructive molecule.

These results cannot be explained by the presence of a contaminating population of p75-immunoreactive crest cells that were present in the NEP cell cultures, for several reasons. NEP cells were cultured 48 hours and stained for p75-immunoreactivity, and only cultures that had no p75-immunoreactive cells (100% of cultures) were analyzed. P75-immunonegative cells readily generated mixed clones that included p75-immunoreactive cells, indicating that p75-negative cells could generate p75$^+$ crest-like cells. P75-immunoreactive cells could constitute 80% of the cultured population within two days of BMP treatment, and this large increase was not due to proliferation of crest cells, since BMP had no mitogenic effect on either NEP cells or on neural crest cells. Taken together, these data strongly suggest that NEP cells are capable of generating neural crest and its derivatives.

Figure 4:
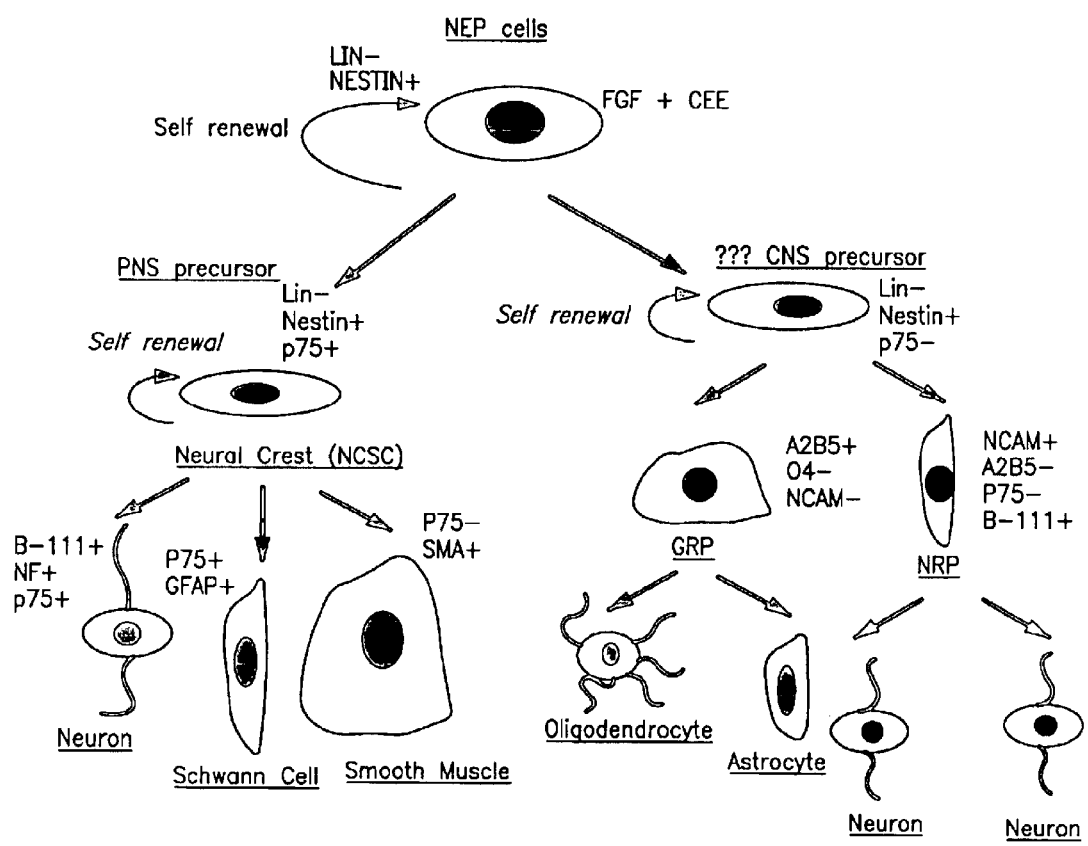
FIG. 4 shows a summary of the immunoreactivities of NEP cells and their progeny, including neural crest stem cells and derivative cells of the peripheral nervous system.

In U.S. Ser. No. 08/852,744, a model was proposed for NEP cell differentiation (FIG. 1), wherein it was argued that NEP cell differentiation occurs via a progressive restriction in developmental fate, as has been suggested for neural crest differentiation. D. J. Anderson, 3 Neuron 1–12, supra. It was suggested that NEP cells will generate CNS derivatives via intermediate, more-restricted precursors termed NRP's and GRP's. Subsequently, the existence of such precursors was demonstrated, and it was shown that NRP and GRP cells can be distinguished from NEP cells by the expression of characteristic markers. U.S. Ser. Nos. 08/909,435; 08/980, 850. NCSCs could be considered similar to other intermediate precursors, since they can be generated from NEP cells and have lost the ability to differentiate into CNS derivatives. The model for NEP cell differentiation has therefore been extended to include differentiation into neural crest (FIG. 4).

These results suggest that while p75-immunoreactive cells do not differentiate into CNS derivatives, a similar limitation in differentiation potential for spinal cord derived NEP cells has not occurred. Even cortical stem cells isolated at a later stage in development are also capable of generating neural crest derivatives. Cortical stem cells harvested at E14.5, a time period well after cranial neural crest has migrated, generated neural crest-like cells, indicating that the ability to generate neural crest may persist far longer than previously supposed. It should be noted that both reported stem cell populations were maintained in FGF. EGF-dependent neurosphere stem cells and adult neurosphere stem cells, which appear similar to embryonic neurospheres in most characteristics, have not been shown to generate neural crest.

These results provide a possible origin for the late appearing neural crest population described as emigrating from the dorsal spinal cord as late as E5 in chick embryos. Z. Korade & E. Frank, Restriction in Cell Fates of Developing Spinal Cord Cells Transplanted to Neural Crest Pathways, 16 J. Neurosci. 7638–7648 (1995); G. S. Sohal et al., DiI Labeling and Homeobox Gene Islet-1 Expression Reveal the Contribution of Ventral Neural Tube Cells to the Formation of the Avian Trigeminal Ganglion, 14 Int. J. Dev. Neurosci. 419–427 (1996). These results suggest that after neural tube closure, some spinal cord cells are capable of generating peripheral derivatives and that these derivatives are an important component of normal development. Taken together with the present results, these experiments suggest that mouse and rat neural crest differentiation may be similar to chick crest development. It further suggests that the late appearing population of crest cells does not represent a segregated population of stem cells. Rather, they represent a normal differentiation potential of the CNS stem cell under appropriate environmental signals.

The present experiments suggest that BMP-2 may be important in regulating the differentiation of NEP cells into NCSC's. BMP-2 significantly increased the number of p75-immunoreactive NCSC's present in culture. The increase in crest cell number was not due to an increase in proliferation, since BMP-2 appeared to be an antitnitotic agent and significantly reduced the number of dividing cells present. Rather, BMP-2 appeared to act as an instructive molecule to promote crest differentiation without cell division. Similar effects have been show with BMP-4 and BMP-7. See, Hazel et al., Soc. Of Neurosci. Abstr. 131.9 (1997). Explant experiments with chick neural tubes, Dickinson et al., supra; Liem et al., supra; K. F. Liem, Jr. et al., A Role for the Roof Plate and its Resident TGF beta-related Proteins in Neuronal Patterning in the Dorsal Spinal Cord, 91 Cell 127–138 (1997), as well as experiments studying crest differentiation in Xenopus embryos have also implicated ectoderm and members of the TGF-β superfamily in promoting neural crest differentiation. P. A. Wilson & A. Hemmati-Brivanlou, Induction of Epidermis and Inhibition of Neural Fate by BMP-4, 376 Nature 331–333 (1995); R. Mayor et al., Role of FGF and Noggin in Neural Crest Induction, 189 Dev. Biol. 1–12 (1997); A. Mancilla & R. Mayor, Neural Crest Formation in Xenopus laevis: Mechanisms of Xslug Induction, 177 Dev. Biol. 580–589 (1996). Thus, the available data suggest that members of the TGF-β superfamily present either in the dorsal tube or the overlying ectoderm may be important instructive molecules that regulate crest differentiation. Several members of the family include dorsalin, K. Basler et al., Control of Cell Pattern in the Neural Tube: Regulation of Cell Differentiation by Dorsalin-1, A Novel TGF beta Family Member, 73 Cell 687–702 (1993), TGF-β, Liem et al., (1997), supra, are expressed at the appropriate times in vivo and therefore represent likely candidates. Other molecules such as noggin and slug may also play a role. The present NEP cell-crest cell culture assay represents a simple assay in which such molecules can be rapidly tested.

The demonstration that a significant proportion of NEP stem cells can generate neural crest and that this number can be regulated by BMP provides a potential source for large numbers of crest cells for analysis. Historically, harvesting and analyzing neural crest cells has been difficult, since they are present only transiently in early embryonic development. Further, the average yield of crest cells from a single E10.5 rat neural tube is only 100–150 neural crest cells. In contrast, each neural tube harvested at the same stage yields about 100,000 cells, of which potentially 60% are stem cells. Furthermore, CNS stem cells can be maintained over multiple passages, further amplifying the number of available stem cells. Generating neural crest cells from culture CNS stem cells represents a novel method of obtaining very large numbers of PNS derivatives.

In summary, these results establish a lineage relationship between a CNS stem cell (the NEP cell) and a PNS stem cell (the NCSC). Differentiation of one stem cell into another has been demonstrated, and this differentiation is regulated by external signals, such as BMP-2. These results further the understanding of the sequential restriction in developmental potential of precursor cells and provide a model to analyze the molecular events underlying differentiation of NCSC from embryonic neural stem cells.

Expression of EGF Receptor and FGF Receptor Isoforms During NEP Stem Cell Differentiation Differentiated cells of the spinal cord arise from initially pluripotent NEP cells via the generation of lineage restricted precursors with more limited differentiation potential. Two restricted precursors, a neuron-restricted precursor (NRP; U.S. Ser. No. 08/909,435, hereby incorporated by reference) that can generate multiple kinds of neurons, and a glial restricted precursor (GRP; U.S. Ser. No. 08/980,850, hereby incorporated by reference) that can generate oligodendrocytes and astrocytes, have been described. NEP cells, GRPs, and NRPs all require fibroblast growth factor (FGF) for their survival or differentiation in culture. The absolute requirement for FGF for NEP cell growth and proliferation is in sharp contrast to the requirements of multipotent neural stem cells (neurospheres) from other brain regions. Reynolds et al., supra; Reynolds & Weiss, supra; Vescovi et al., supra. Neurosphere stem cells do not require FGF, but require epidermal growth factor (EGF) for their survival or proliferation either in vivo or in vitro, though FGF may act synergistically with EGF to promote mitosis. Gritti et al., supra; Vescovi et al., supra. NEP stem cells, on the other hand, are FGF-dependent, and no effect of EGF has been discovered. Failure of NEP cells to respond to EGF could reflect absence or low levels of EGF receptor (EGF-R), though the presence or absence of EGF-R on NEP cells remains to be determined.

While EGF may not act on NEP cells, both EGF and FGF likely act at multiple stages in the CNS neural differentiation process, and their effects may be stage specific and dose dependent. At low doses, FGF is a survival factor for stem cells, while at high doses FGF appears to be a mitogen. Further, at low doses FGF biases differentiation towards neurons, while at higher doses appears to promote astrocyte differentiation. X. Qian et al., FGF2 Concentration Regulates the Generation of Neurons and Glia from Multipotent Cortical Stem Cells, 18 Neuron 81–93 (1997). High doses of FGF also inhibit oligodendrocyte differentiation, R. Bansal & S. E. Pfeiffer, FGF-2 Converts Mature Oligodendrocytes to a Novel Phenotype, 50 J. Neurosci. Res. 215–228 (1997), and expression of a dominant negative form of FGF will prevent oligodendrocyte migration and alter myelination. D. Harari et al., FGF Plays a Subtle Role in Oligodendrocyte Maintenance In Vivo, 49 J. Neurosci. Res. 404–415 (1997); D. J. Osterhout et al., Transplanted Oligodendrocyte Progenitor Cells Expressing a Dominant-Negative FGF Receptor Transgene Fail to Migrate In Vivo, 17 J. Neurosci. Res. 9122–9132 (1997). Likewise, EGF can inhibit differentiation of restricted O2A precursors, H. Z. Sheng et al., Epidermal Growth Factor Inhibits the Expression of Myelin Basic Protein in Oligodendrocytes, 23 J. Neurosci. Res. 425–432 (1989), and overexpression of the EGF-R may bias precursor cells towards an astrocytic fate. R. C. Burrows et al., Response Diversity and the Timing of Progenitor Cell Maturation Are Regulated by Developmental Changes in EGFR Expression in the Cortex, 19 Neuron 251–267 (1997); L. Lillien, Changes in Retinal Cell Fate Induced by Overexpression of EGF Receptor, 377 Nature 158–162 (1995). EGF and FGF also act as survival factors for postmitotic neurons. D. Casper et al., EGF Enhances the Survival of Dopamine Neurons in Rat Embryonic Mesencephalon Primary Cell Culture, 30 J. Neurosci. Res. 372–381 (1991). Thus, the effect of FGF and EGF depends on the concentration applied and the stage of cell differentiation at which it is presented.

The effects of EGF are mediated by a 170 kDa receptor tyrosine kinase named EGF-R. TGF-alpha, a structurally related polypeptide, can bind and activate EGF-R with similar molecular weights as EGF. EGF-R expression has been localized to the germinal zone both postnatally as well as in late embryonic development. M. R. Kaser et al., Comparison between Epidermal Growth Factor, Transforming Growth Factor-alpha and EGF Receptor Levels in Regions of Adult Rat Brain, 16 Brain Res. Mol. Brain Res. 316–322 (1992); H. I. Kornblum et al., Prenatal Ontogeny of the Epidermal Growth Factor Receptor and its Ligand, Transforming Growth Factor Alpha, in the Rat Brain, 380 J. Comp. Neurol. 243–261 (1997); K. B. Seroogy et al., Proliferative Zones of Postnatal Rat Brain Express Epidermal Growth Factor Receptor mRNA, 670 Brain Res. 157–164 (1995). Expression of FGF is mediated via activation of different members of the FGF receptor (FGF-R) family. D. M. Ornitz et al., Receptor Specificity of the Fibroblast Growth Factor Family, 271 J. Biol. Chem. 15292–15297 (1996). Four separate FGF receptors (FGF-Rs1–4) and a variety of splice variants have been identified. D. Givol & A. Yayon, Complexity of FGF Receptors: Genetic Basis for Structural Diversity and Functional Specificity, 6 FASEB J. 3362–3369 (1992); D. E. Johnson & L. T. Williams, Structural and Functional Diversity in the FGF Receptor Multigene Family, 60 Adv. Cancer Res. 1–41 (1993). FGF-Rs 1–4 bear strong homology to each other, but bind different FGFs with varying degrees of affinity. Ornitz et al., supra. Alternative MRNA splicing events produce isoforms of FGF-Rs that have unique ligand binding properties. T. Miki et al., Determination of Ligand-Binding Specificity by Alternative Splicing: Two Distinct Growth Factor Receptors Encoded by a Single Gene, 89 Proc. Nat'l Acad. Sci. USA 246–250 (1992); W. Werner et al., Differential Splicing in the Extracellular Region of Fibroblast Growth Factor Receptor 1 Generates Receptor Variants with Different Ligand-Binding Specificities, 12 Mol. Cell. Biol. 82–88 (1992). One splicing event that results from exclusion of exons encoding the extracellular amino-terminal regions produces either a "short" form of the receptor, which contains two Ig-like domains in its extracellular region, or a "long" form, which contains three Ig-like domains. Another splicing event involves the usage of two alternate exons for the C-terminal regions of the third Ig-like domain and results in three distinct versions of this domain (IIIa, IIIb, or IIIc) in FGF-Rs 1, 2, or 3. FGFR-4 is not know to be alternatively spliced in this region. Different isoforms show different ligand affinities and may differentially activate different second messenger pathways. Thus, knowing which splice variant is expressed by a particular cell may allow prediction on actions of different FGFs on neural precursor cells.

In situ hybridization analysis and immunohistochemistry have clearly shown that both EGF and many different members of the FGF family are present during embryonic development of the CNS. L. M. Lazar & M. Blum, Regional Distribution and Developmental Expression of Epidermal Growth Factor and Transforming Growth Factor-alpha mRNA in Mouse Brain by a Quantitative Nuclease Protection Assay, 12 J. Neurosci. 1688–1697 (1992); R. P. Schaudies et al., Epidermal Growth Factor Immunoreactive Material in the Rat Brain: Localization and Identification of Multiple Species, 250 J. Biol. Chem. 10447–10450 (1989); J. H. Fallon et al., Epidermal Growth Factor Immunoreactive Material in the Central Nervous System: Location and Development, 224 Science 1107–1109 (1984); K. Kuzis et al., Developmental Time Course of Acidic and Basic Fibroblast Growth Factors' Expression in Distinct Cellular Populations of the Rat Central Nervous System, 358 J. Comp. Neurol. 142–153 (1995). EGF expression has been detected in the developing brain and in the adult. Further, EGF-R knockout shows a cortical phenotype, D. W. Threadgill et al., Targeted Disruption of Mouse EGF Receptor: Effect of Genetic Background on Mutant Phenotype, 269 Science 230–234 (1995) with cortical dysgenesis, neuronal ectopias, and reduced numbers of astrocytes. Astrocytes and neurons both synthesize EGF, but which cells synthesize EGF at early embryonic ages remains to be determined. Multiple FGFs are also present in the CNS. At least ten different FGFs have been identified, and several FGFs, including FGFs 1, 2, 4, 5, and 8, may be present at different stages of development and may play different roles. M. Heikinheimo et al., FGF-8 Expression in the Post-Gastrulation Mouse Suggests Roles in the Development of the Face, Limbs and Central Nervous System, 48 Mech. Dev. 129–138 (1994); Kuzis et al., supra; A. Orr-Urtreger et al., Developmental Localization of the Splicing Alternatives of Fibroblast Growth Factor Receptor-2 (FGFR2), 158 Dev. Biol. 475–486 (1993). Acidic and basic FGF (FGF1 and FGF2, respectively) are likely very important in early CNS development. Both of these FGFs are present in the developing spinal cord, though the cells that synthesize acidic and basic FGFs have not been identified. Basic FGF expression is detected as early as E1–5., with acidic FGF being detected at a somewhat later stage. M. D. Ford et al., Co-localization of FGF-2 and a Novel Heparin Sulphate Proteoglycan in Embryonic Mouse Brain, 5 Neuroreport 565–568 (1994). Neutralizing antibodies to FGF block neurogenesis, Y. Tao et al., In Vivo Neurogenesis is Inhibited by Neutralizing Antibodies to Basic Fibroblast Growth Factor, 33 J. Neurobiol. 289–296 (1997), suggesting that FGF synthesized in the developing nervous system is important for normal development.

To understand the multiple actions of EGF and FGF on neural stem cells and their differentiated progeny, characterization of the EGF and FGF receptor subtypes present in the neural precursor cells has begun. It is shown herein that NEP cells express a subset of FGF-Rs, but do not respond to EGF or express EGF-R. The pattern of expression of FGF-Rs on NEP cells is distinct from that on NRPs, GRPs, oligodendrocytes, and astrocytes. It s also shown that NEP cells synthesize both acidic and basic FGF and that autocrine loop allows cell survival independent of exogenously added FGF.

EXAMPLE 25
FGF but Not PDGF, EGF or NGF, Acts as a Mitogen in NEP Cell Cultures It has previously been shown herein that NEP cells isolated from E10.5 neural tubes are pluripotent cells capable of differentiating into neurons, astrocytes, and oligodendrocytes, and that NEP cells require FGF and CEE to remain undifferentiated and proliferative in culture. To determine whether other cytokines could substitute for CEE or FGF, the mitotic effects of a variety of factors known to be expressed at this stage of development were examined.

NEP cells prepared according to Example 1 were grown in NEP medium and pulsed with BRDU for a period of 4 hours. Cells were fixed with formaldehyde (4%), permeabilized with HCl, neutralized with sodium borate, and reacted with an anti-BRDU labeled antibody to identify labeled cells as described above. Dividing cells were estimated by counting five random fields from each 35 mm dish. Duplicate dishes were examined from each experiment, and each experiment was repeated three times. Of all the factors tested, only FGF acted as a mitogen. None of PDGF, EGF, or NGF had any effect at any dose tested. Basic FGF (bFGF), however, was mitogenic as assessed by BRDU incorporation at doses as low as 0.10 ng/ml, with a maximal effect seen at 10 ng/ml. Acidic FGF (aFGF) was equipotent. Subsequent experiments with FGF were performed at 20 ng/ml unless otherwise stated.

EXAMPLE 26
FGF as a Mitogen in NEP Cell Cultures

The failure to see an effect of EGF, either alone or synergistically with FGF (Example 25), was surprising given previous results that growth of EGF-dependent stem cells could be supported by FGF and vice versa. Therefore, expression by NEP of the EGF-R by reverse transcriptase-polymerase chain reaction (RT-PCR) and immunocytochemistry was examined.

Total RNA was isolated from cells by a modification of the guanidine isothiocyanate-phenol-chloroform extraction method (TRIZOL; GIBCO/BRL). Then, cDNA was synthesized using 1–5 µg of total RNA in a 20 µl reaction volume according to methods well known in the art. SUPERSCRIPT II (GIBCO/BRL), a modified Maloney murine leukemia virus reverse transcriptase and oligo(dT)12–18 primers were used, and the GIBCO/BRL protocol was followed. For PCR, aliquots of cDNA, equivalent to 1/20 of the above cDNA synthesis reaction, were used in a 50 µl reaction volume. PCR amplification of the receptor mRNAs was performed using ELONGASE polymerase (GIBCO/BRL). Primer sequences used for PCR amplification of the receptor mRNAs are shown in Table 10.

TABLE 10

| Gene | Size (bp) | Primers (sense, antisense) |
|---|---|---|
| FGFR-1 | 764 | SEQ ID NO:1, SEQ ID NO:2 |
| FGFR-2 (bek) | 339 | SEQ ID NO:3, SEQ ID NO:4 |
| FGFR-2 (KGF) | 319 | SEQ ID NO:5, SEQ ID NO:6 |
| FGFR-3 | 600 | SEQ ID NO:7, SEQ ID NO:8 |
| FGFR-4 | 672 | SEQ ID NO:9, SEQ ID NO:10 |
| aFGF | 437 | SEQ ID NO:11, SEQ ID NO:12 |
| bFGF | 344 | SEQ ID NO:13, SEQ ID NO:14 |
| EGF | 569 | SEQ ID NO:15, SEQ ID NO:16 |
| EGFR | 205 | SEQ ID NO:17, SEQ ID NO:18 |
| PDGFR-α | 331 | SEQ ID NO:19, SEQ ID NO:20 |
| FGFR (common) | 341 | SEQ ID NO:21, SEQ ID NO:22 |
| FGFR1-P1 (rat) | 989, 732 | SEQ ID NO:23, SEQ ID NO:24 |
| FGFR1-P1 (human) | 828, 1095 | SEQ ID NO:25, SEQ ID NO:26 |

The reactions were run for 35 cycles, and a 10 minute incubation at 72° C. was added at the end to ensure complete extension. The PCR products were purified using ADVANTAGE PCR-PURE KIT (Clontech, Palo Alto, Calif.) and used for sequence analysis, restriction endonuclease digest reactions, subcloning, and slot blot experiments, infra.

Acutely dissociated cells were obtained following enzymatic digestion and trituration of E10.5 cells from caudal neural tube as described above. Individual NEP cells were identified and carefully aspirated into a pipette containing 2 µl of a reverse transcription solution [50 mM KCl, 10 mM Tris-HCl, 5 mM MgCl$_2$, 1 mM of each dNTP, 50 ng oligo-dT primer, RNase inhibitor, reverse transcriptase (SUPERSCRIPT II, GIBCO/BRL)] under visual control. The contents of the pipette were then transferred to a tube containing 20 µl of the reverse transcription solution and incubated at 42° C. for 1 hour. One tenth of this cDNA was used for a subsequent PCR reaction using specific primers listed in Table 10.

EGF-R could not be detected by either RT-PCR or by immunocytochemistry in sections or in dissociated culture. The failure to detect EGF-R could not be attributed to the sensitivity of the methods, since EGF-R was readily detected in astrocytes, neurons, and oligodendrocyte cultures. Thus, NEP cells do not respond to exogenous EGR because they lack EGF-R (erbB-1).

EXAMPLE 27
E10.5 Neuroepithelium Expresses Multiple FGF Receptor (FGFR) Types The results of Examples 25 and 26 showed that FGF, but not EGF or any other mitogen tested was a critical mitogen for NEP stem cells. To determine which FGF receptors mediate the effects of FGF, the expression of individual FGFRs were evaluated in both mass culture and by single cell analyses. The expression of the four major FGF receptors, as well as their splice variants were examined by PCR and splice specific restriction digests. PCR primers were designed to amplify a region of each receptor that encompassed the distal half of exon III from FGF-R1 and FGF-R3. For FGF-R2, individual primers were designed to specifically amplify either bek (the IIIc isoform) or KGFR (the IIIb isoform) for technical reasons. A single set of primers was used for FGF-R4, since this receptor is not alternatively spliced in this region. The primer sequences are listed in Table 10. PCR under these conditions amplified products of the expected size, and their identities were confirmed by sequence analysis. Sequence analysis was performed by cloning PCR fragments into pBLUESCRIPT KS+ (Stratagene, La Jolla, Calif.) and sequencing by the dideoxy method, according to methods well known in the art. FGF-R1, FGF-R3, and FGF-R4 and the IIIc isoform of FGF-R2 were present. The bek isoform was absent and could not be detected even after additional amplification cycles, though bek isoforms were readily detected from the whole embryos at the same stage.

To distinguish between the IIIb and IIIc forms of FGFR-1 and FGFR-3, restriction digest reactions were performed on the PCR products using enzymes specific to each form of both receptors. To discriminate between IIIb and IIIc-specific PCR products, restriction endonuclease digests were performed with VspI (GIBCO/BRL) and AccI (GIBCO/BRL) for FGFR-1 and BalI (GIBCO/BRL) and BspMI (New England Biolabs) for FGFR-3 according to manufacturer's instrulctions. The VspI and BalI endonucleases uniquely cut the amplified products from the IIIb variants of FGFR-1 and FGFR-3, respectively, and the AccI and BspMI enzymes uniquely cut the amplified products from the IIIc variants of FGFR-1 and FGFR-3, respectively. The resulting fragments were resolved on 1.5% agarose gels stained with ethidium bromide and photographed under UV illumination.

Only the enzymes specific for the IIIc forms of FGFR-1 and FGFR-3 digest products amplified form E10.5 neuroepithelium. Only the IIIb isoforms could be detected in E10.5 neural tubes or cultured NEP cells. IIIb isoforms are present in the skin, demonstrating the reliability of the assay. Thus, NEP cells express a restricted subset of FGFR receptors, FGFR-1 (IIIc), bek, FGFR-3 (IIIc), and FGFR-4 are all expressed, while the IIIb forms of FGFR-1, FGFR-2 (KGFR), and FGFR-3 are not.

EXAMPLE 28
Individual NEP Cells at E10.5 Express the Same Subset of FGF Receptors It was previously shown herein that NEP cells are homogeneous in their morphology, differentiation potential, and antigens expressed. The results with mass cultures of RT-PCR for FGF-Rs expressed by NEP cells suggested that multiple FGF-Rs are expressed by individual NEP cells. It was possible, however, that individual NEP cells are heterogeneous and express a subset of the FGF-Rs detected in mass. To assess whether single NEP cells express all four FGF-Rs, NEP cells were plated at low density and isolated single cells by aspiration under microscopic control. Single cell cDNA was prepared from individual cells using labeled nucleotides, and the labeled cDNA was hybridized to slot blots containing FGF-R cDNA, actin, and GFAP according to methods well known in the art.

Briefly, equimolar amounts of rat FGF-Rs 1, 2(bek), 3, and 4, as well as β-actin (for a positive control) and GFAP (for a negative control) were blotted on ZETA PROBE membrane (BioRad, Richmond, Calif.) following a 10-minute incubation under denaturing conditions. These were then individually probed with a $10^5$–$10^6$ cpm RNA probe transcribed from each of the FGF-R plasmids using T7 RNA polymerase. The hybridization mixture contained 5×SSC, 2×Denhardt's solution, 50% formamide, and 100 μg/ml yeast tRNA. Following a 4-hour pre-hybridization and overnight hybridization at 61° C., the blots were washed at a final concentration of 2×SSC/0.2% SDS and exposed to autoradiographic film for 12 hours with an intensifying screen. At this level of stringency, there was little or no cross hybridization of the individual probes with any of the other FGF-Rs.

For single cell analysis, individual cells were identified and carefully asprirated into a pipette containing 2 μl of a reverse transcriptase mixture as described above. Following the single strand cDNA synthesis, a second strand was synthesized by the addition of a solution containing 100 mM KCl, 20 mM Tris-HCl, 5 mM $MgCl_2$, 10 mM ammonium sulfate, 1 mM ATP, 5, μg BSA, 1 unit T4 ligase, 1 unit RNase H, and 20 units T4 DNA polymerase 1 (final volume 80 μl) to the RT reaction. The entire mixture was then incubated at 12° C. for 1 hour, then at 22° C. for 1 hour, and then blunt-ended with the addition of 10 units T4 DNA polymerase and 10 units of the Klenow fragment of DNA polymerase I. The double-stranded cDNA was then purified by ethanol precipitation, phenol-chloroform extraction, and drop analysis. RNA was synthesized using 4 μl of transcription buffer (GIBCO/BRL; 200 mM Tris-HCl, pH 8.0, 40 mM $MgCl_2$, 10 mM spermidine-$(HCl)_3$, 125 mM NaCl), 10 mM DTT, 0.5 mM of each rNTP, 20 units RNase inhibitor, 5, μl cDNA template, 2000 units T7 RNA polymerase, and 50 mCi of 32P-α-CTP in a total volume of 20 μl. The reaction was then incubated at 37° C. for 4 hours and then ethanol precipitated. This RNA was then used as a probe to detect individual FGF receptors on the previously made slot blots.

Labeled probe from a single cell showed specific hybridization to FGFR-1, FGFR-2, FGFR-3, and FGFR-4, but not to GFAP, which is not detectable in NEP cells and served as a negative control. All single cells analyzed (n=5) expressed all four FGFRs, indicating that the mass culture results reflect the profile seen in single cells. To rule out the possibility that the FGF result was due to cross hybridization of the labeled probe to closely related FGFR sequences, radiolabeled probe was prepared and hybridized in slot blots. Probes to individual FGFRs did not show any significant cross hybridization under the conditions of the experiment. The results of these control experiments confirm the expression of all four receptors by individual cells of E10.5 neuroepithelium.

EXAMPLE 29
Neuroepithelial Stem Cells Express Only the Long Isoform of FGFR-1

In addition to the IIIb and IIIc isoforms, alternative splicing produces FGF-R1 molecules with 2 or 3 Ig-like domains, called "short" or "long" forms, respectively. J. Hou et al., Fibroblast Growth Factor Receptors from Liver Vary in Three Structural Domains, 251 Science 665–668 (1991); Johnson & Williams, supra. The biological significance of the differential expression of these isoforms is not yet clear, although it has been shown that the long isoform of FGF-R1 traffics to a perinuclear locale, while the short isoform does not. I. A. Prodovsky et al., the Nuclear Trafficking of Extracellular Fibroblast Growth Factor (FGF)-1 Correlates with the Perinuclear Association of the FGF Receptor-1a Isoforms but Not the FGF Receptor-1B Isoforms, 271 J. Biol. Chem. 14198–14205 (1995). In addition, the examination of several types of cancers has revealed the preferential expression of the short isoform of FGF-R1, with the degree of malignancy correlating with the ratio of the short to the long isoform being expressed. F. Penault-Llorca et al., Expression of FGF and FGF Receptor Genes in Human Breast Cancer, 61 Int. J. Cancer 170–176 (1995); These findings suggest that he differential expression of FGF-R1 isoforms are important in regulating the proliferative potential fo the cells on which they are expressed.

To determine which form of FGF-R1 is expressed in E10.5 NEP cells, primers that amplify the extracellular domain of FGF-R1 encompassing the second and third Ig-like domains were designed. A 1-kb product indicated the expression of the long isoform, while a 732 bp product was amplified from transcripts of the short isoform. Astrocytes, as well as malignant glioma cells, expressed both the long and short isoforms, as well as the third isoform with a 200 bp deletion. In contrast, NEP cells express only the long isoform of FGF-R1. These results suggest that it is not the short form of FGF-R1 receptor that is important for proliferation in these cells.

EXAMPLE 30
NEP Cells Express Multiple FGF Receptors at Varying Levels

Although most FGF ligands are able to activate most FGF receptors, the simultaneous expression of several FGFRs during embryonic development suggests distinct functions of the signal mediated by each receptor.

To estimate the relative levels of FGF-R expression in NEP cells, a single PCR primer pair was designed to amplify conserved sequences in the tyrosine kinase domain of each of the four FGF-Rs. This domain is highly conserved, both across species (rat, mouse, and human), as well as across receptors. The single primer pair was used to amplify a 341 bp product, a combination of all expressed receptors. Restriction digestion analyses were then done to distinguish between four receptors. Enzymes used and the expected sizes of the digested products are listed in Table 11. The samples were then resolved on a 10% non-denaturing 1XTBE polyacrylamide gel. Gels were then stained with ethidium bromide, and images were captured using a Kodak Digital Science Camera. The Kodak DS program was used to calculate the relative intensities of each band.

TABLE 11

| PCR Product | Enzyme | Fragment Sizes (bp) |
|---|---|---|
| FGF-R1 IIIb | VspI | 374, 390 |
| FGF-R-1 IIIc | AccI | 309, 455 |
| FGF-R3 IIIb | BalI | 290, 310 |
| FGF-R3IIIc | BspMI | 289, 211 |
| FGF-R common | | |
| R-1 specific | SmaI | 239, 102 |
| R-2 specific | EcIHK | 214, 127 |
| R-3 specific | | |

In a preliminary analysis of the relative expression level of each receptor in NEP cells, FGFR-4 is the least abundant of the expressed receptors.

EXAMPLE 31
FGF-R and EGF-R Receptor Expression is Altered During Maturation of NEP Cells The results presented herein showed that EGF-R is not expressed by NEP stem cells. EGF-R, however, has been shown to be expressed by multiple cell types later in development. Therefore, the differentiated progeny of NEP cells were examined for EGF-R expression. NEP cells and O2A precursor cells did not express detectable levels of EGF-R. In contrast, NRPs, neurons, and astrocytes expressed EGF-R. Thus, cells acquire EGF-R expression in culture soon after differentiation, consistent with the timing of EGF-R expression in vivo.

The FGF-R expression on NEP cells was also compared with the pattern of FGF-Rs on differentiated progeny. NEP cells, NCAM+ neuroblasts, astrocytes, and oligdendrocytes were harvested at early developmental stages and purified populations were obtained by differential antibody selection. FGF-R expression was tested as described above with multiple independent cDNA preparations. NEP cells had the broadest spectrum of FGF-Rs of all cells analyzed, and each differentiated phenotype expressed a smaller subset of these receptors.

EXAMPLE 32
NEP Cells Synthesize FGFs and do not Require Exogenous FGF when Plated at High Densities It is known in the art that both acidic and basic FGFs are synthesized by cells of the developing neural tube. Results presented herein suggest that at this stage the neural tube is a homogeneous population of NEP stem cells. This raises the possibility that NEP cells not only express multiple FGF-Rs, but that they also synthesize the appropriate ligands. To test this possibility, NEP cells were isolated from E10.5 neural tubes according to the procedure of Example 1 and examined for FGF1 and FGF2 expression by RT-PCR according to the method of Example 26. Both FGF1 and FGF2 are present in NEP cells. The specificity of the PCR product was confirmed by restriction digestion and by sequencing of the amplified product, confirming that the FGF expression described by in situ hybridization was due to expression in NEP cells. To determine if the FGF synthesized was available to activate FGF-Rs and maintain NEP cells proliferation, NEP cells were plated at differing densities in the absence of FGF and measured BRDU incorporation. Plating at high densities mimicked the effect of FGF on cell proliferation and at such high densities virtually all cells had divided with the time period assayed. To test whether the effect of high density was due to endogenous FGF, the effect of FGF on BRDU incorporation was assessed in the presence of neutralizing antibodies to bFGF. Neutralizing antibodies to bFGF reduced proliferation by 50% (at maximal doses), and this effect could be antagonized by adding excess acidic FGF, showing that at least part of the proliferative response was due to FGF. Adding neutralizing antibodies to both acidic and basic FGF did not decrease the proliferation rate further, suggesting that either other mitogenic factors are secreted or FGF does not have to be released for its mitogenic effect. L. Sherman et al., Expression of Multiple Forms of bFGF in Early Avian Embryos and Their Possible Role in Neural Crest Cell Commitment, 638 Ann. N.Y. Acad. Sci. 470–473 (1991).

FGFs have been shown to be important in neural tube induction and in the survival and proliferation of a variety of cell types. T. M. Lamb & R. M. Harland, Fibroblast Growth Factor is a Direct Neural Inducer, Which Combined with Noggin Generates Anterior-Posterior Neural Pattern, 121 Development 3627–3636 (1995); K. Launay et al., A Truncated FGF Receptor Blocks Neural Induction by Endogenous Xenopus Inducers, 122 Development 869–880 (1996); M. Murphy et al., Fibroblast Growth Factor Stimulates the Proliferation and Differentiation of Neural Precursor Cells In Vitro, 25 J. Neurosci. Res. 463–475 (1990); P. Walicke et al., Fibroblast Growth Factors Promote Survival or Dissociated Hippocampal Neurones and Enhances Neurite Extension, 84 Proc. Nat'l Acad. Sci. USA 5459–5463 (1986). The results presented herein extend these observations and show that FGFs are important in stem cell proliferation and differentiation. NEP cells express a subset of FGF-Rs, but do not express EGF-R or PDGR-Rs. The pattern of expression of FGF-Rs on NEP cells is distinct from that on NRPs, GRPs, oligodendrocytes, and astrocytes. The instant results further show that NEP cells, in addition to expressing appropriate receptors, synthesize both acidic and basic FGF and that autocrine loop allows cell survival independent of exogenously added FGF.

An important observation presented herein is that NEP cells do not express EGF-R. Failure to detect EGR-R was not due to the sensitivity of the methods used, since EGF-R expression was readily detected in other cell types, both by immunocytochemistry and PCR. Absence of EGF-R expression on NEP cells is consistent with these results. That EGF alone has no effect on embryonic spinal cord stem cell proliferation or survival. Recent in situ hybridization data also suggests that EGF-R expression is seen only in later stages of development. The instant results are also consistent with results from EGF-R knockout mice, which do not show any abnormality in stem cell proliferation or survival, though they do demonstrate cortical dysgenesis at later developmental stages. These results clearly illustrate the distinction between cortical EGF-dependent neurosphere cells and FGF-dependent NEP stem cells. V. Tropepe & D. van der Kooy, Differential Roles of EGF and FGR2 in Proliferation May Reflect Separate Neural Stem Cell Subpopulations, 23 Soc. Neurosci. Abstr. 131.3 (1997); A. Represa et al., Is There a Lineage Relationship between bFGF- and EGF-Responsive Stem Cells in the Spinal Cord?, 23 Soc. Neurosci. Abstr. 131.14 (1997).

These results also show that PDGFR-alpha and -beta are not present on NEP cells though neuroblasts and glioblasts express these receptors at later stages in development, K. K. Johe et al., Single Factors Direct the Differentiation of Stem Cells from the Fetal and Adult Central Nervous System, 10 Genes Dev. 3129–3140 (1996); N. P. Pringle et al., PDGF Receptors in the Rat CNS: During Late Neurogenesis, PDGF Alpha-Receptor Expression Appears to be Restricted to Glial Cells of the Oligodendrocyte Lineage, 115 Development 535–551 (1992); B. P. Williams et al., A PDGF-Regulated Immediate Early Gene Response Initiates Neuronal Differentiation in Ventricular Zone Progenitor Cells, 18 Neuron 553–562 (1997), and are consistent with the present results the PDGF has no effect on NEP cells. PDGF has previously been shown to act on cortical stem cells (presumably neurosphere cells) as an instructive molecule to bias precursor cell differentiation into neurons. E. J. Williams et al., Activation of the FGF Receptor Underlies Neurite Outgrowth Stimulated by L1, N-CAM, and N-Cadherin, 13 Neuron 583–594 (1994). The absence of PDGF-R further illustrate the difference between NEP cells and cortical EGF-dependent neurospheres. The instant results, taken together with previous results on the trophic requirements of EGF-dependent neurospheres, provides further evidence that two distinct classes of stem cells are present in the caudal neural tube. An EGF-dependent, EGF-R-negative stem cell that is present early in embryonic development and that survives in small numbers in the adult animal, J. Santa-Olalla & L. Covarrubias, Epidermal Growth Factor (EF), Transforming Growth Factor-alpha (TGF-alpha), and Basic Fibroblast Growth Factor (bFGF) Differentially Influence Neural Precursor Cells of Mouse Embryonic Mesencephalon, 42 J. Neurosci. Res. 172–183 (1995), and an EGF-responsive stem cell that is present later in embryonic development and can also be detected in adult animals. Equally important, the present results suggest that EGF-R immunoreactivity may be used to select different populations of stem cells. Whether these results can be generalized to the cortex remains to be determined, though both EGF-dependent and FGF-dependent stem cells have been described in adult animals.

While EGF has no effect on NEP cells, and NEP cells do not express EGF-R, several different FGF-Rs are detectable. The IIIc isoform of FGF Rs1–3, as well as FGF-R4, are all present on NEP cells. Analysis of the relative levels of FGF-Rs further suggest that FGF-R2 is the most abundant. These results are consistent with in situ experiments that show that FGF-R1 and FGF-R2 are exrpessed at E8.5 in mouse (equivalent to E10.5 in rats). FGF-R3 is also expressed in the ventricular zone of the developing spinal cord, a site where proliferating NEP cells are present, providing independent confirmation of the present results. The expression of FGF-R4 has not been described in the developing nervous system. It has been shown herein, however, that both protein and message for FGF-R4 can be detected in cultured neuroepithelial cells. More recent reports have documented expression of FGF-R4 in the adult brain and in the developing nervous system of the zebra fish embryo. B. Thisse et al., Novel FGF Receptor (Z-FGFR4) is Dynamically Expressed in Mesoderm and Neuroectorderm During Early Zebrafish Embryogenesis, 203 Dev. Dynamics 377–391 (1995). Consistent with these observations are studies examining the expression of FGF-R4 expression in ES cell differentiation. Neuronal differentiation of an ES cell line results in increased levels of FGF-R4 receptor. The presence of FGF-R4 on NEP cells and not on differentiated progeny identifies a unique marker for NEP cells that may be used for isolating purified populations of stem cells.

Comparison of the expression of FGF receptors on NEP cells and differentiated progeny suggests that NEP cells express a large subset of FGF-R isoforms, while each different subtype expresses a subset of these receptors. The present results on the spectrum of FGF-R on GRPs are similar to the results previously reported, Bansal et al., Regulation of FGF Receptors in the Oligodendrocyte Lineage, 7 Mol. Cell. Neurosci. 263–275 (1996), on the FGF-Rs present on O2A precursors (a related glial precursor cell). FGF-R3 expression has been localized to neurons at later stages of development. K. Peters et al., Unique Expression Pattern of the FGF Receptor 3 Gene During Mouse Organogenesis, 155 Dev. Biol. 423–430 (1993). The present results extend these results to show that neuronal precursors also express FGF-R3. The stage-specific expression of subsets of receptors raises the possibility that stage-specific responses to FGF may be mediated by the complement of receptors expressed rather than different FGF ligands. While speculative, the demonstrated ability to isolate these populations of cells allows direct addressing of this possibility. Equally important to the ability to type cells by the subset of FGF-R expressed provides additional independent markers for cell type specification. Indeed, FGF-R3 expression has been used to distinguish type 1 astrocytes from type 2 astrocytes.

Binding affinities of the various subtypes of receptors have been directly compared. Ornitz et al., supra. While some controversy exists on the binding specificity of different FGF receptor isoforms, M. Mathieu et al., Receptor Binding and Mitogenic Properties of Mouse Fibroblast Growth Factor 3, 270 J. Biol. Chem. 24197–24203 (1995); Ornitz et al., supra; J. Partanen et al., FGFR-4, a Novel Acidic Fibroblast Growth Factor Receptor with a Distinct Expression Pattern, 10 EMBO J. 1347–1354 (1991), the pattern of expression of the IIIc isoforms of FGF-Rs 1, 2, and 3 on NEP cells suggest that acidic and basic FGFs would be the best mitogens for NEP cells. FGF3 and FGF7, which bind predominantly to the IIIb isoforms, are unlikely to be important. Indeed, expression analysis shows that two of the FGFs that preferentially activate the subset of receptors present on NEP cells are expressed at the appropriate time in development. The present analysis of FGF1 and FGF2 expression shows that NEP cells synthesize both ligands. The concentration of ligands is sufficient to maintain NEP cell proliferation independent of exogenously added FGF, and blocking antibodies to bFGF reduce cell division. Thus, an autocrine loop likely exists in vivo to regulate precursor cell number.

FGF receptors are though to activate multiple signally pathways downstream, and the specific downstream signals activated depend on the ligand present, its binding affinity to the receptor subtype expressed, and the state of differentiation of the cells. The present results show that FGFs are critical regulators of spinal cord stem cell proliferation and differentiation. The action of FGFs is mediated by multiple FGF-Rs, and the specificity of action of FGF is likely due to the specific subset of receptors expressed by a particular cell type.

In summary, to characterize the role of EGF and FGF in regulating neuroepithelial stem cell differentiation, the expression of FGF, EGF, and their receptors by NEP cells and their derivatives was examined. Using reverse transcriptase polymerase chain reaction (RT-PCR) using cDNA from purified cultures or single cells, it was shown that undifferentiated neuroepithelial cells express a subset of FGF receptor isoforms, but do not express the EGF-R (erb-1). Comparison of the FGF receptor pattern of expression of differentiated neurons and glial cells with that of neuroepithelial cells suggests that FGF-R4 is uniquely expressed on neuroepithelial cells. FGF-R1 is expressed by neuroepithelial cells, and its expression is maintained by neurons, while FGF-R2 is downregulated. The pattern of expression of FGF receptors in recently differentiated astrocytes, oligodendrocytes, and GRP cells is distinct from that of neuroepithelial cells and neurons. Expression of FGF and EGF by NEP cells was also examined. NEP cells express detectable levels of both FGF1 and FGF2, but no detectable levels of EGF. The expression of FGF-1 and FGF-2 is likely biologically relevant, since cells grown at high density do not require FGF for their survival, and cell grown in the presence of neutralizing antibodies to FGF show a reduction in cell survival and division. Thus, neuroepithelial cells synthesize and respond to FGF, but not to EGF, and are distinct from EGF neurospheres. Their pattern of expression of FGF isoforms may serve to distinguish NEP cells from their more differentiated progeny.

All of the references cited herein and not previously expressly incorporated by reference are hereby incorporated by reference.

We claim:

1. A method for generating mammalian neural crest stem cells comprising:
    (a) obtaining mammalian, p75 immunonegative neuroepithelial stem cells derived from the neural tube from a mammalian embryo at a stage of embryonic development after closure of the neural tube by:
        (i) removing a sample of neural tube tissue from a mammal at a stage of embryonic development after closure of the neural tube;
        (ii) dissociating cells comprising the sample of neural tube tissue removed from the mammal;
        (iii) plating the dissociated cells in feeder-cell-independent culture on a substratum and in a media comprising fibroblast growth factor and chick embryo extract; and
        (iv) identifying p75 immunonegative cells via immunohistochemistry and obtaining the mammalian, p75 immunonegative neuroepithelial stem cells;
    (b) harvesting the mammalian, p75 immunonegative neuroepithelial stem cells by trypsinization; and
    (c) replating the harvested mammalian, p75 immunonegative neuroepithelial stem cells onto a fibronectin substrate and in a media comprising chick embryo extract, NGF, FGF and EGF to generate p75 immunoreactive, neural crest stem cells.

2. A method for generating rat neural crest stem cells comprising:
    (a) obtaining rat, p75 immunonegative neuroepithelial stem cells derived from the neural tube from a rat embryo at a stage of embryonic development after closure of the neural tube by:
        (i) removing a sample of neural tube tissue from a rat at a stage of embryonic development after closure of the neural tube;
        (ii) dissociating cells comprising the sample of neural tube tissue removed from the rat;
        (iii) plating the dissociated cells in feeder-cell-independent culture on a substratum and in a media comprising fibroblast growth factor and chick embryo extract so that rat neuroepithelial stem cells are obtained; and (iv) identifying p75 immunonegative cells via immunohistochemistry and obtaining the mammalian, p75 immunonegative neuroepithelial stem cells;

(b) harvesting the rat, p75 immunonegative neuroepithelial stem cells by trypsinization; and (c) replating the harvested rat, p75 immunonegative neuroepithelial stem cells onto a fibronectin substrate and in a media comprising chick embryo extract, NGF, FGF, and EGF to generate rat, p75 immunoreactive, neural crest stem cells.

3. A method for isolating mammalian neural crest stem cells comprising:

(a) generating neural crest stem cells in accordance with the method of claim 1; and (b) isolating the neural crest stem cells via antibody capture with an antibody against neurotrophin receptor p75.

4. A method for isolating rat neural crest stem cells comprising:

(a) generating rat neural crest stem cells in accordance with the method of claim 2; and (b) isolating the rat neural crest stem cells via antibody capture with an antibody against neurotrophin receptor p75.

* * * * *

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
      (A) LENGTH: 23
      (B) TYPE: nucleic acid
      (C) STRANDEDNESS: single
      (D) TOPOLOGY: linear (xi) SEQUENCE DESCRIPTION: SEQ ID NO:1:

TGGGAGCATC AACCACACCT ACC                                                  23

(2) INFORMATION FOR SEQ ID NO:2:

(i) SEQUENCE CHARACTERISTICS:
      (A) LENGTH: 19
      (B) TYPE: nucleic acid
      (C) STRANDEDNESS: single
      (D) TOPOLOGY: linear (xi) SEQUENCE DESCRIPTION: SEQ ID NO:2:

GCCCGAAGCA GCCCTCGCC                                                      19

(2) INFORMATION FOR SEQ ID NO:3:

(i) SEQUENCE CHARACTERISTICS:
      (A) LENGTH: 23
      (B) TYPE: nucleic acid
      (C) STRANDEDNESS: single
      (D) TOPOLOGY: linear (xi) SEQUENCE DESCRIPTION: SEQ ID NO:3:

GTCGTTGAAC GTTCACCACA CCG                                                23

(2) INFORMATION FOR SEQ ID NO:4:

(i) SEQUENCE CHARACTERISTICS:
      (A) LENGTH: 20
      (B) TYPE: nucleic acid
      (C) STRANDEDNESS: single (D) TOPOLOGY: linear (xi) SEQUENCE DESCRIPTION: SEQ ID NO:4:

GCAGAACTGT CAACCATGCA                                             20

(2) INFORMATION FOR SEQ ID NO:5:

(i) SEQUENCE CHARACTERISTICS:
        (A) LENGTH: 23
        (B) TYPE: nucleic acid
        (C) STRANDEDNESS: single
        (D) TOPOLOGY: linear (xi) SEQUENCE DESCRIPTION: SEQ ID NO:5:

GTCGTTGAAC GTTCACCACA CCG                                         23

(2) INFORMATION FOR SEQ ID NO:6:

(i) SEQUENCE CHARACTERISTICS:
        (A) LENGTH: 20
        (B) TYPE: nucleic acid
        (C) STRANDEDNESS: single
        (D) TOPOLOGY: linear (xi) SEQUENCE DESCRIPTION: SEQ ID NO:6:

CAGGCAGACT GGTTGGCCTG                                             20

(2) INFORMATION FOR SEQ ID NO:7:

(i) SEQUENCE CHARACTERISTICS:
        (A) LENGTH: 22
        (B) TYPE: nucleic acid
        (C) STRANDEDNESS: single
        (D) TOPOLOGY: linear (xi) SEQUENCE DESCRIPTION: SEQ ID NO:7:

AGCTTGGTCA TGGAAAGTGT GG                                          22

(2) INFORMATION FOR SEQ ID NO:8:

(i) SEQUENCE CHARACTERISTICS:
        (A) LENGTH: 24
        (B) TYPE: nucleic acid
        (C) STRANDEDNESS: single
        (D) TOPOLOGY: linear (xi) SEQUENCE DESCRIPTION: SEQ ID NO:8:

ACGGTGGGCG AGCCCAAGCC CTTC                                        24

(2) INFORMATION FOR SEQ ID NO:9:

(i) SEQUENCE CHARACTERISTICS:
        (A) LENGTH: 20
        (B) TYPE: nucleic acid
        (C) STRANDEDNESS: single
        (D) TOPOLOGY: linear (xi) SEQUENCE DESCRIPTION: SEQ ID NO:9:

ATCGGAGGCA TTCGGCTGCG                                             20

(2) INFORMATION FOR SEQ ID NO:10:

(i) SEQUENCE CHARACTERISTICS:
        (A) LENGTH: 20
        (B) TYPE: nucleic acid
        (C) STRANDEDNESS: single
        (D) TOPOLOGY: linear (xi) SEQUENCE DESCRIPTION: SEQ ID NO:10:

AGAACTGCCG GGCCAAAGGG                                            20

(2) INFORMATION FOR SEQ ID NO:11:

(i) SEQUENCE CHARACTERISTICS:
        (A) LENGTH: 19
        (B) TYPE: nucleic acid
        (C) STRANDEDNESS: single
        (D) TOPOLOGY: linear (xi) SEQUENCE DESCRIPTION: SEQ ID NO:11:

TGAAGGGGAG ATCACAACC                                             19

(2) INFORMATION FOR SEQ ID NO:12:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO:12:

GAAACAAGAT GGCTTTCTGG C                                          21

(2) INFORMATION FOR SEQ ID NO:13:

(i) SEQUENCE CHARACTERISTICS:
        (A) LENGTH: 22
        (B) TYPE: nucleic acid
        (C) STRANDEDNESS: single
        (D) TOPOLOGY: linear (xi) SEQUENCE DESCRIPTION: SEQ ID NO:13:

AAGCGGCTCT ACTGCAAGAA CG                                         22

(2) INFORMATION FOR SEQ ID NO:14:

(i) SEQUENCE CHARACTERISTICS:
        (A) LENGTH: 22
        (B) TYPE: nucleic acid
        (C) STRANDEDNESS: single
        (D) TOPOLOGY: linear (xi) SEQUENCE DESCRIPTION: SEQ ID NO:14:

TTCTGTCCAG GTCCCGTTTT GG                                         22

(2) INFORMATION FOR SEQ ID NO:15:

(i) SEQUENCE CHARACTERISTICS:
        (A) LENGTH: 22
        (B) TYPE: nucleic acid
        (C) STRANDEDNESS: single
        (D) TOPOLOGY: linear (xi) SEQUENCE DESCRIPTION: SEQ ID NO:15:

CGTTGGACAA CTCCCCTAAG GC                                         22

(2) INFORMATION FOR SEQ ID NO:16:

(i) SEQUENCE CHARACTERISTICS:
        (A) LENGTH: 19
        (B) TYPE: nucleic acid
        (C) STRANDEDNESS: single
        (D) TOPOLOGY: linear (xi) SEQUENCE DESCRIPTION: SEQ ID NO:16:

CATGCACACG CCACCATTG                                                19

(2) INFORMATION FOR SEQ ID NO:17:

(i) SEQUENCE CHARACTERISTICS:
        (A) LENGTH: 32
        (B) TYPE: nucleic acid
        (C) STRANDEDNESS: single
        (D) TOPOLOGY: linear (xi) SEQUENCE DESCRIPTION: SEQ ID NO:17:

GCTGGGGAAG AGGAGAGGAG AACGAGTGGT GG                                 32

(2) INFORMATION FOR SEQ ID NO:18:

(i) SEQUENCE CHARACTERISTICS:
        (A) LENGTH: 11
        (B) TYPE: nucleic acid
        (C) STRANDEDNESS: single
        (D) TOPOLOGY: linear (xi) SEQUENCE DESCRIPTION: SEQ ID NO:18:

GCAGGTGTCT T                                                        11

(2) INFORMATION FOR SEQ ID NO:19:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO:19:

CTGTAACTGG CAGGCTCGGA G                                             21

(2) INFORMATION FOR SEQ ID NO:20:

(i) SEQUENCE CHARACTERISTICS:
        (A) LENGTH: 23
        (B) TYPE: nucleic acid
        (C) STRANDEDNESS: single
        (D) TOPOLOGY: linear (xi) SEQUENCE DESCRIPTION: SEQ ID NO:20:

GTTGTCTGCA GTACAAGTTG GCG                                           23

(2) INFORMATION FOR SEQ ID NO:21:

(i) SEQUENCE CHARACTERISTICS:
        (A) LENGTH: 22
        (B) TYPE: nucleic acid
        (C) STRANDEDNESS: single
        (D) TOPOLOGY: linear (xi) SEQUENCE DESCRIPTION: SEQ ID NO:21:

TCAGTGAGAT GGAGATGATG AA                                            22

(2) INFORMATION FOR SEQ ID NO:22:

(i) SEQUENCE CHARACTERISTICS:
        (A) LENGTH: 24
        (B) TYPE: nucleic acid
        (C) STRANDEDNESS: single
        (D) TOPOLOGY: linear (xi) SEQUENCE DESCRIPTION: SEQ ID NO:22:

```
CCAAAGTCAC TGCAGTATCT TCAT                                                                        24
```

(2) INFORMATION FOR SEQ ID NO:23:

(i) SEQUENCE CHARACTERISTICS:
        (A) LENGTH: 20
        (B) TYPE: nucleic acid
        (C) STRANDEDNESS: single
        (D) TOPOLOGY: linear (xi) SEQUENCE DESCRIPTION: SEQ ID NO:23:

```
GCCACTCTCT GCACTGCCAG                                                                             20
```

(2) INFORMATION FOR SEQ ID NO:24:

(i) SEQUENCE CHARACTERISTICS:
        (A) LENGTH: 22
        (B) TYPE: nucleic acid
        (C) STRANDEDNESS: single
        (D) TOPOLOGY: linear (xi) SEQUENCE DESCRIPTION: SEQ ID NO:24:

```
GTTACCCGCC AAGCACGTAT AC                                                                          22
```

(2) INFORMATION FOR SEQ ID NO:25:

(i) SEQUENCE CHARACTERISTICS:
        (A) LENGTH: 24
        (B) TYPE: nucleic acid
        (C) STRANDEDNESS: single
        (D) TOPOLOGY: linear (xi) SEQUENCE DESCRIPTION: SEQ ID NO:25:

```
CGAGCTCACT GTGGAGTATC CATG                                                                        24
```

(2) INFORMATION FOR SEQ ID NO:26:

(i) SEQUENCE CHARACTERISTICS:
        (A) LENGTH: 22
        (B) TYPE: nucleic acid
        (C) STRANDEDNESS: single
        (D) TOPOLOGY: linear (xi) SEQUENCE DESCRIPTION: SEQ ID NO:26:

```
GTTACCCGCC AAGCACGTAT AC                                                                          22
```